United States Patent
Wang

(10) Patent No.: US 8,180,134 B2
(45) Date of Patent: May 15, 2012

(54) IN VIVO STRUCTURAL AND FLOW IMAGING

(75) Inventor: Ruikang K. Wang, Portland, OR (US)

(73) Assignee: Oregon Health & Science University, Portland, OR (US)

(*) Notice: Subject to any disclaimer, the term of this patent is extended or adjusted under 35 U.S.C. 154(b) by 471 days.

(21) Appl. No.: 12/442,928

(22) PCT Filed: Sep. 18, 2007

(86) PCT No.: PCT/US2007/078743
§ 371 (c)(1),
(2), (4) Date: Mar. 25, 2009

(87) PCT Pub. No.: WO2008/039660
PCT Pub. Date: Apr. 3, 2008

(65) Prior Publication Data
US 2010/0027857 A1 Feb. 4, 2010

Related U.S. Application Data

(60) Provisional application No. 60/909,242, filed on Mar. 30, 2007, provisional application No. 60/826,998, filed on Sep. 26, 2006.

(51) Int. Cl.
*G06K 9/00* (2006.01)
(52) U.S. Cl. .................................... 382/131; 382/130
(58) Field of Classification Search ........... 382/128–134
See application file for complete search history.

(56) References Cited

U.S. PATENT DOCUMENTS

| 6,549,801 | B1 | 4/2003 | Chen |
| 2003/0199769 | A1 | 10/2003 | Podoleanu |
| 2003/0199796 | A1 | 10/2003 | Yamazaki et al. |
| 2003/0220749 | A1 | 11/2003 | Chen et al. |
| 2005/0004453 | A1 | 1/2005 | Tearney et al. |
| 2005/0140984 | A1 | 6/2005 | Hitzenberger |
| 2005/0171438 | A1* | 8/2005 | Chen et al. ............... 600/476 |

(Continued)

FOREIGN PATENT DOCUMENTS

WO WO2004043245 A 5/2004

OTHER PUBLICATIONS

Sarunic, Marinko V. et al. "Real-time Quadrature Projection Complex Conjugate Resolved Fourier Domain Optical Coherence Tomography," Optics Letters, 31, pp. 2426-2428 (2006), Optical Society of America, Washington, DC.

(Continued)

*Primary Examiner* — David Mis
(74) *Attorney, Agent, or Firm* — Schwabe, Williamson & Wyatt

(57) ABSTRACT

Embodiments of the present invention include but are not limited to methods and systems for optical coherence imaging. A method for optical coherence imaging may comprise scanning a sample with an incident beam from a light source; detecting one or more spectral interference signals from the sample; modulating the one or more spectral interference signals by a linear translation of a reference mirror while scanning the sample in a cross-sectional direction; and obtaining at least one image of the sample from the modulated one or more spectral interference signals, the at least one image including a selected one of a full range structural image of the sample and a separated structure/flow image of the sample.

29 Claims, 21 Drawing Sheets

U.S. PATENT DOCUMENTS

2006/0270929 A1  11/2006  Bouma et al.

OTHER PUBLICATIONS

Vakoc, B.J. et al., Elimination of Depth Degeneracy in Optical Frequency-domain Imaging Through Polarization-based Optical Demodulation, Optics Letters, 31, pp. 362-364 (2006), Optical Society of America, Washington, DC.

Bachmann, Adrian H. et al., "Heterodyne Fourier Domain Optical Coherence Tomography for Full Range Probing with High Axial Resolution," Optics Express 14 (4): pp. 1487-1496, Feb. 20, 2006.

Ma, Zhen et al., "Arbitrary Three-phase Shifting Algorithm for Achieving Full Range Spectral Optical Coherence Tomography," Chinese Physics Letters 23 (2): pp. 366-369, Feb. 2006.

Yasuno, Yoshiaki, et al., "Real Time and Full-Range Complex Fourier Domain Optical Coherence Tomography," Optical and Quantum Electronics 37 (13-15), pp. 1157-1163, Dec. 2005.

Sarunic, Marinko et al., "Instantaneous Complex Conjugate Resolved Spectral Domain and Swept-source OCT Using 3×3 Fiber Couplers," Optics Express 13, pp. 957-967 (2005).

Huber, R., et al., "Amplified, Frequency Swept Lasers for Frequency Domain Reflectometry and OCT Imaging: Design and Scaling Principles," Optics Express 13 (9), pp. 3513-3528, May 2, 2005.

Gotzinger, Erich, et al., "High Speed Full Range Complex Spectral Domain Optical Coherence Tomography," Optics Express 13 (2), pp. 583-594, Jan. 24, 2005.

Zhang, Jun, et al., "Full Range Polarization-sensitive Fourier Domain Optical Coherence Tomography," Optics Express 12 (24), pp. 6033-6039, Nov. 29, 2004.

Yun, S, et al., "Removing the Depth-degeneracy in Optical Frequency Domain Imaging with Frequency Shifting," Optics Express 12, pp. 4822-4828, 2004.

Wojtkowski, M. et al., "Full Range Complex Spectral Optical Coherence Tomography Technique in Eye Imaging," Optics Letters 27 (16) pp. 1415-1417, Aug. 15, 2002, Optical Society of America, Washington, DC.

Leitgeb, Rainer A., et al., "Phase-shifting Algorithm to Achieve High-speed Long-depth-range Probing by Frequency-domain Optical Coherence Tomography," Optics Letters 28 (22), pp. 2201-2203, Nov. 15, 2003, Optical Society of America, Washington, DC.

Hitzenberger, Christoph K., et al., "Differential Phase Measurements in Low-Coherence Interferometry Without 2 pi Amgbiguity," Optics Letters 26 (23), pp. 1864-1866, Dec. 1, 2001, Optical Society of America, Washington, DC.

Choma, Michael A., et al., "Doppler Flow Imaging of Cytoplasmic Streaming Using Spectral Domain Phase Microscopy," Journal of Biomedical Optics 11 (2), Article No. 024014, Mar.-Apr. 2006.

Seki, J., et al., "Velocity Profiles in the Rat Cerebral Microvessels Measured by Optical Coherence Tomography," Clinical Hemorheology and Microcirculation 34 (1-2), pp. 233-239, 2006.

Leitgeb, Rainer A. et al., "Real-time Measurement of In Vitro Flow by Fourier-domain Color Doppler Optical Coherence Tomography," Optics Letters 29 (2), pp. 171-173, Jan. 15, 2004, Optical Society of America, Washington, DC.

Leitgeb, Rainer A. et al., "Real-time Assessment of Retinal Blood Flow with Ultrafast Acquisition by Color Doppler Fourier Domain Optical Coherence Tomography," Optics Express 11 (23), pp. 3116-3121, Nov. 17, 2003.

Ahn, Yeh-Chan, et al., "Investigation of Laminar Dispersion with Optical Coherence Tomography and Optical Doppler Tomography," Optics Express 13 (20), pp. 8164-8171, Oct. 3, 2005.

Zhang, Jun, et al., "In Vivo Blood Flow Imaging by a Swept Laser Source Based Fourier Domain Optical Doppler Tomography," Optics Express 13 (19), pp. 7449-7457, Sep. 19, 2005.

Pedersen Cameron J., et al., "Phase-referenced Doppler Optical Coherence Tomography in Scattering Media," Optics Letters 30 (16), pp. 2125-2127, Aug. 15, 2005, Optical Society of America, Washington, DC.

Vakoc, B.J., et al., "Phase-resolved Optical Frequency Domain Imaging," Optics Express 13 (14), pp. 5483-5493, Jul. 11, 2005.

Wang, Ruikang K. et al., "Three-dimensional Optical Microangiography Maps Directional Blood Perfusion Deep Within Microcirculation Tissue Beds In Vivo," Physics in Medicine and Biology, 52 (2007) N531-N537, IOP Publishing Ltd.

Wang, Ruikang K. et al., "Three Dimensional Optical Angiography," Optics Express vol. 15, No. 7, pp. 4083-4097, Apr. 2, 2007.

Yasuno, Y et al. "Simultaneous B-M-Mode Scanning Method for Real-Time Full-Range Fourier Domain Optical Coherence Tomography", Applied Optics, OSA, Optical Society of America, Mar. 10, 2006, pp. 1861-1865, XP001241180, ISSN: 0003-6935, Washington, DC, US.

Wojtkowski, M. et al. "Real-Time In Vivo Imaging by High-Speed Spectral Optical Coherence Tomography", Optics Letters, OSA, Optical Society of America, Oct. 1, 2003, pp. 1745-1747, vol. 28, No. 19, XP002272407, ISSN: 0146-9592, Washington, DC, US.

Wojtkowski, M et al. "In Vivo Human Retinal Imaging by Fourier Domain Optical Coherence Tomography", Journal of Biomedical Optics, SPIE, Jul. 2002, pp. 457-463, vol. 7, No. 3, XP002272406, ISSN: 1083-3668, Bellingham, WA, US.

Shuliang, J. et al. "Simultaneous Acquisition of Sectional and Fundus Ophthalmic Images With Spectral-Domain Optical Coherence Tomography", Optics Express, Jan. 24, 2005, pp. 444-452, vol. 13, No. 2, XP002463448.

* cited by examiner

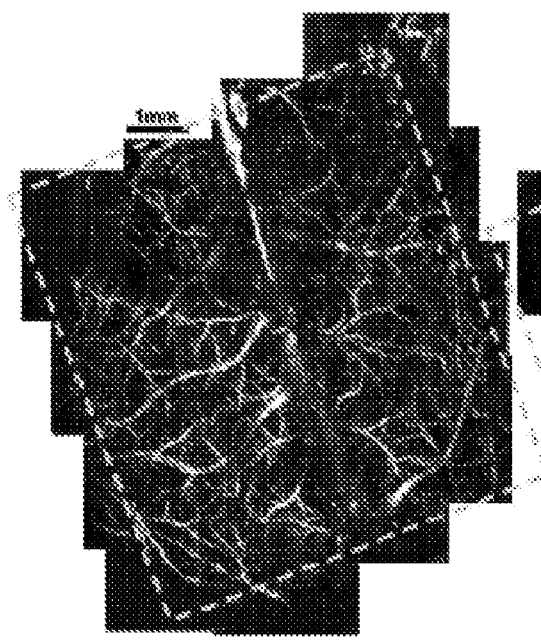 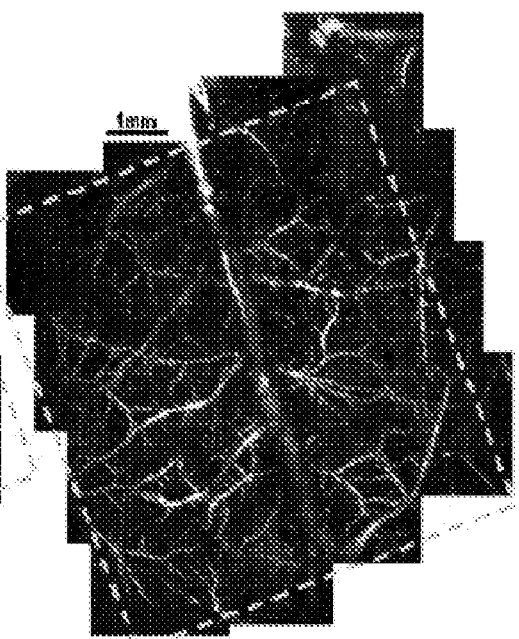
FIGURE 14A　　　FIGURE 14B
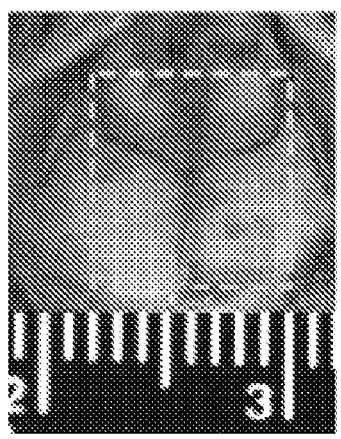 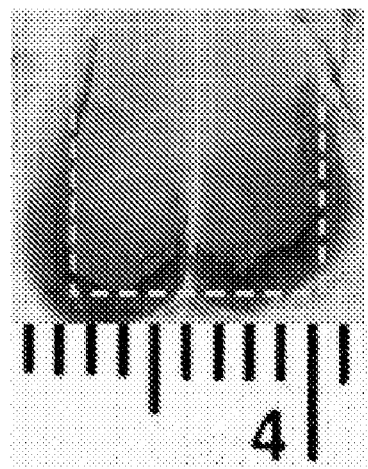
FIGURE 14C　　　FIGURE 14D

IN VIVO STRUCTURAL AND FLOW IMAGING

CROSS-REFERENCE TO RELATED APPLICATIONS

The present application claims priority to provisional application 60/826,998, filed Sep. 26, 2006, and provisional application 60/909,242, filed Mar. 30, 2007. The disclosures of the provisional applications are hereby incorporated in their entirety, except for those sections, if any, that are inconsistent with this specification.

TECHNICAL FIELD

Embodiments of the invention relate generally to the field of biomedical imaging, specifically to methods, apparatuses, and systems associated with optical coherence tomographic and optical angiographic imaging.

BACKGROUND

In vivo three-dimensional mapping of biologic tissue and vasculature is a challenging proposition due to the highly-scattering and absorptive nature of biologic tissue. Some current methods have slow scanning speeds making in vivo three-dimensional imaging difficult. Some other techniques having faster scanning speeds are still lacking due to their inability to scan deeply into biologic tissue without producing overlapped images, requiring the use of invasive procedures to scan the tissue of interest. For example, in some cases, the skull must be removed or substantially thinned in order to scan deep brain vasculature. Moreover, techniques aimed at deeper imaging generally cannot provide deep imaging of tissue having moving material (e.g., blood flow). Therefore, methods to effectively image structure and/or tissue movement, such as blood flow, are of substantial clinical importance.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIGS. 14A and 14B illustrate projection views of blood perfusion of a mouse brain before and after, respectively, the right carotid artery was blocked, imaged using methods in accordance with various embodiments of the present invention; FIG. 14C illustrates the mouse brain with the skin folded aside and FIG. 14D illustrates the mouse brain with the skull removed for comparison to the imaged results;

FIG. 16A shows the imaging result when the projection of the flow vector in the capillary tube onto the optical axis is toward the probe beam incident direction, and FIG. 16B shows the same result but with the flow in the capillary tube reversed;

FIG. 17A provides a direct intensity x-y projection map where directional flow information may not be inferred; FIG. 17B provides a bi-directional flow projection map obtained by fusing the flow image representing the velocity vector projecting onto the optical axis pointing toward the incident beam direction with the flow image pointing away from the incident beam direction; FIG. 17C provides a 3-D volume-rendered bi-directional flow image together with micro-structural images (bounded on the three sides as shown) that may be used to infer the flow directions in 3-D space with the coordinate definition given in FIG. 17D;

DETAILED DESCRIPTION OF EMBODIMENTS OF THE INVENTION

In the following detailed description, reference is made to the accompanying drawings which form a part hereof and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

A phrase in the form of "A/B" means "A or B." A phrase in the form "A and/or B" means "(A), (B), or (A and B)." A phrase in the form "at least one of A, B and C" means "(A), (B), (C), (A and B), (A and C), (B and C) or (A, B and C)." A phrase in the form "(A) B" means "(B) or (A B)," that is, A is optional.

In various embodiments of the present invention, methods, apparatuses, and systems for biomedical imaging are provided. In exemplary embodiments of the present invention, a computing system may be endowed with one or more components of the disclosed articles of manufacture and/or systems and may be employed to perform one or more methods as disclosed herein.

In various embodiments, structure and/or flow information of a sample may be obtained using optical coherence tomography (OCT) (structure) and optical angiography (OAG) (structure and flow) imaging based on the detection of spectral interference. Such imaging may be two-dimensional (2-D) or three-dimensional (3-D), depending on the application. Structural imaging may be of an extended depth range relative to prior art methods, and flow imaging may be performed in real time. One or both of structural imaging and flow imaging as disclosed herein may be enlisted for producing 2-D or 3-D images.

Figure 1:
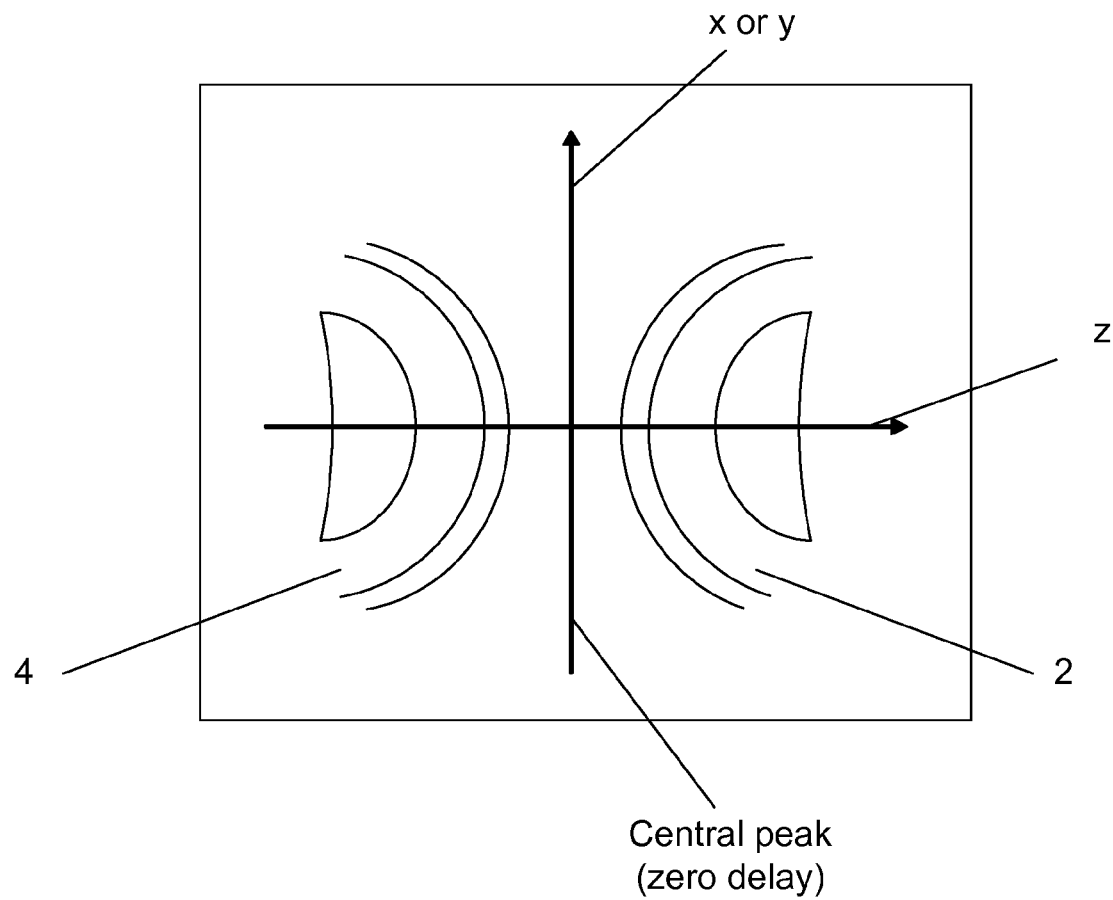
FIG. 1 schematically illustrates an image of an anterior portion of an eye imaged using a prior art method.
Figure 2:
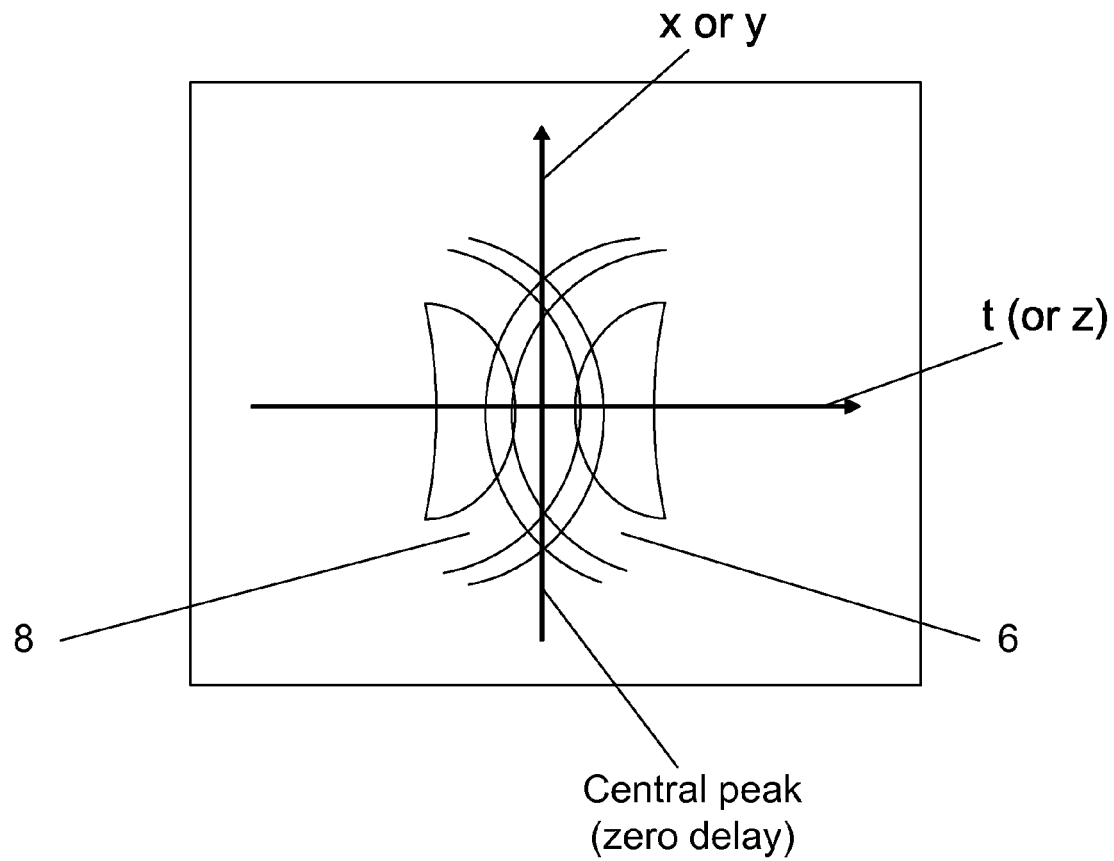
FIG. 2 schematically illustrates an image of an anterior portion of an eye imaged using a prior art method.

Illustrated in FIG. 1 is a depiction of an image resulting from various prior art spectral domain OCT methods. As illustrated, the depicted image is of an anterior chamber of an eye, wherein the right part is the real image 2, while the left part is the mirror image 4. In this example, real image 2 is a distance below the zero delay (to the right in this example) in positive Fourier space. If the surface of the object to be imaged (the anterior chamber in this example) is above the zero delay line (to the left in this example) in negative Fourier space, however, an overlapping problem may occur as illustrated in FIG. 2, wherein the real image 6 overlaps with the mirror image 8. In various embodiments, the object generally must be positioned at some position below the zero delay line in positive Fourier space to avoid overlapping. By doing so, however, the depth range allowing for a cross-sectional image (i.e., the information acquisition range) is narrowed. For example, in some embodiments, the depth range may be narrowed by as much as half.

According to various embodiments of the present invention, a full range complex OCT image may be achieved, with diminished mirror imaging. As used herein, "full range" imaging refers to imaging in the full depth of Fourier space, including both the positive and the negative Fourier spaces.

Figure 3A:
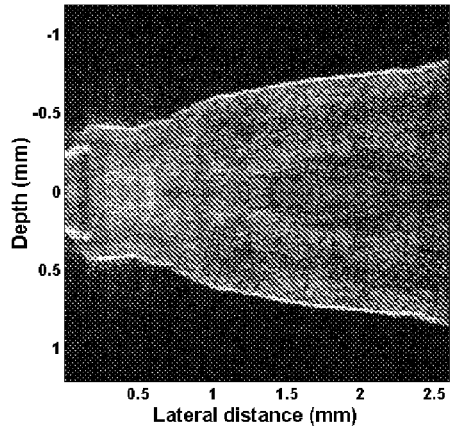
FIG. 3A and FIG. 3B illustrate structure images using imaging methods in accordance with prior art methods.
Figure 3C:
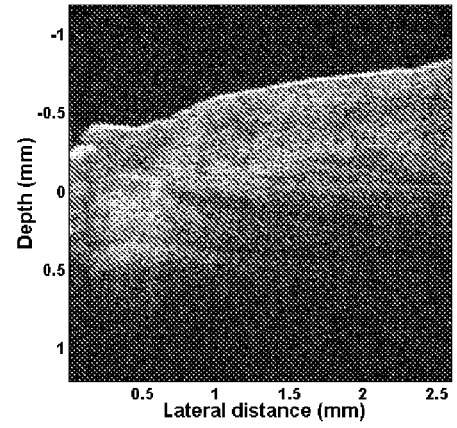
FIG. 3C and FIG. 3D illustrate structure images using imaging methods in accordance with various embodiments of the present invention.
Figure 3B:
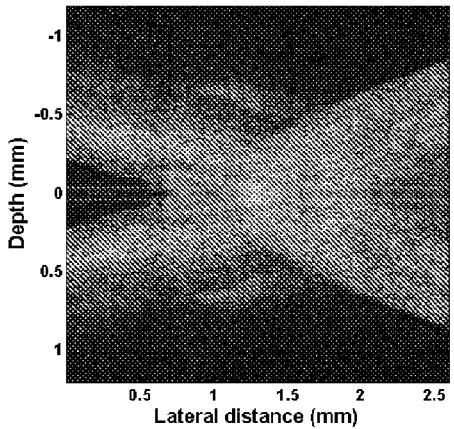
Figure 3D:
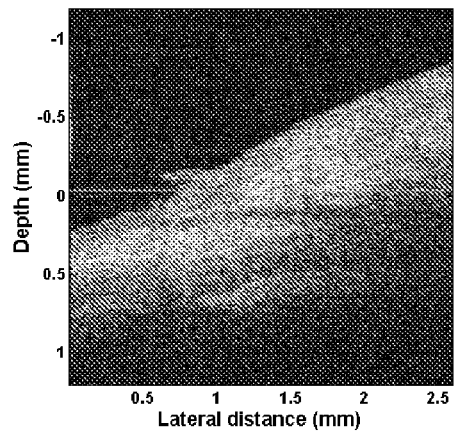

Exemplary images of a human finger are illustrated in FIGS. 3A-3D. As shown in FIG. 3A and FIG. 3B, the images exhibit an overlapping problem similar to the image represented in FIG. 2 using prior art methods. Illustrated in FIG. 3C and FIG. 3D, however, are exemplary images produced in accordance with various embodiments of the present invention. As can be seen, the images are formed in substantially the full depth of Fourier space. In embodiments, such imaging in full Fourier space may be achieved through transformation of a complex function, as opposed to imaging in only half of Fourier space sometimes achieved through transformation of a real-valued function.

According to various embodiments, an OCT image may be obtained by scanning the sample with a sample light in x, y, and λ (λ is sometimes also referred to as the z direction, λ being the representation of z in the wavelength domain) directions to obtain a 3-D spectral interferogram data set, and converting the 3-D spectral interferogram data set from a spectral domain to a time domain to obtain at least one image of the sample. If the sample includes a moving component, the at least one image may comprise a first image and a second image, the first image including static structural information of the sample and the second image including movement information of the sample. If the sample does not include a moving component, the at least one image may comprise a full range structural image of the sample.

Figure 4:
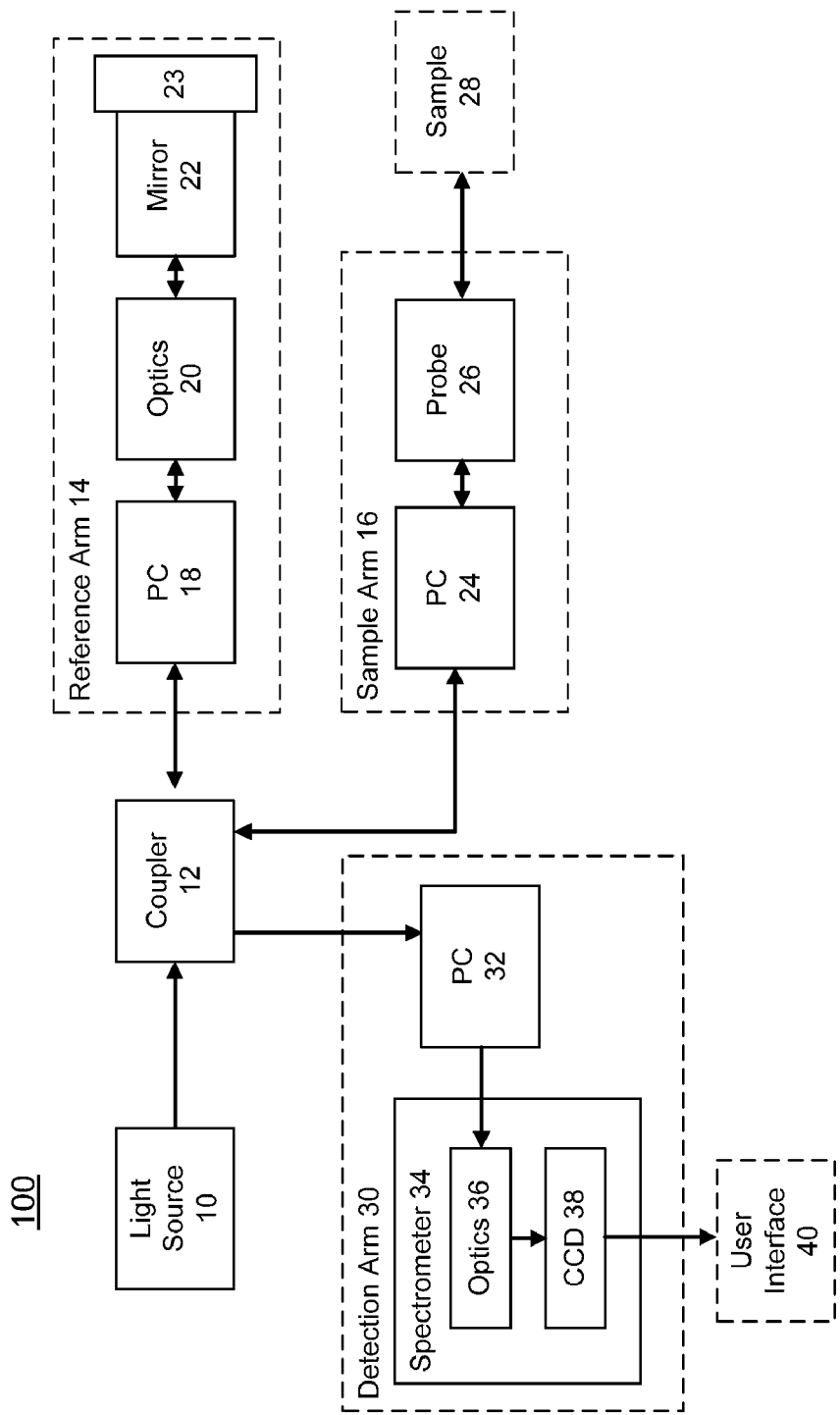
FIG. 4 illustrates an imaging apparatus in accordance with various embodiments of the present invention.

Illustrated in FIG. 4 is an exemplary embodiment of an OCT/OAG apparatus 100 suitable for extended depth range structural and flow imaging, and 2-D and 3-D angiographic imaging. The illustrated OCT/OAG apparatus 100 may include some features known in the art, features which may not be explained in great length herein except where helpful in the understanding of embodiments of the present invention.

As illustrated, OCT/OAG apparatus 100 may include a light source 10. Light source 10 may comprise any light source suitable for the purpose including, but not limited to, a broadband light source or a tunable laser source. A suitable broadband light source may include a superluminescent diode. In one embodiment, light source 10 comprises a superluminescent diode with a central wavelength of 842 nanometers (nm) and a full-width-at-half-maximum bandwidth of 45 nm. In various embodiments, light source 10 may be a light source having one or more longer wavelengths, which may allow for deeper imaging. In various other embodiments, light source 10 may comprise a tunable laser source such as, for example, a swept laser source.

OCT/OAG apparatus 100 may include a fiber coupler 12 for splitting the light from light source 10 into two beams: a first beam provided to a reference arm 14 and a second beam provided to a sample arm 16. In various embodiments, fiber coupler 12 may comprise a 2×2 fiber coupler or any fiber coupler suitable for the purpose.

Sample arm 16 may be configured to provide light from light source 10 to a sample 28 by way of a polarization controller 24 and a probe 26. Probe 26 may include a pair of x-y galvanometer scanners (not illustrated) for scanning sample 28 in an x-y direction. Probe 26 may also comprise the appropriate optics (not illustrated) for delivering the light onto sample 28. In various embodiments, probe 26 may also receive backscattered light from sample 28. Although the characteristics of the light provided to sample 28 may depend on the particular application, in some embodiments, the lateral imaging resolution may be approximately 16 micrometers (μm) determined by an objective lens that focuses light onto sample 28, with a light power on sample 28 being approximately 1 milliwatt (mW).

Reference arm 14 may be configured to provide a reference light to detection arm 30 (discussed more fully below), from the light provided by light source 10, for producing a spectral interferogram in combination with backscattered light from sample 28. Reference arm 14 may include optics 20 and a mirror 22 for reflecting light from light source 10 for providing the reference light. Optics 20 may include, but are not limited to, various lenses suitable for the purpose.

Mirror 22 may be stationary or may be modulated by a modulator 23. Modulation may be equivalent to frequency modulation of the detected signal at detection arm 30. It has been observed that spectral interference signals (interferograms) may be modulated by a constant Doppler frequency, $\omega_0$, by a modulated mirror 22 in the reference arm 14, the modulation making it feasible to separate the moving and static components within sample 28. The spectral interference signal may then be recovered by de-modulating the modulated signal at the modulation frequency, $\omega_0$. De-modulation may be achieved using any suitable method including, for example, a digital or optical de-modulation method. Modulation and de-modulation of spectral interference signals may advantageously improve the signal-to-noise ratio, resulting in an improved image quality for structural, flow, and angiographic imaging.

Various methods may be enlisted for modulating mirror 22. For example, in various embodiments, modulator 23 may be a linear piezo-translation stage onto which mirror 22 is mounted. The piezo-translation stage may be configured to move mirror 22 at some constant velocity across a B-scan (i.e., x direction scan). In an exemplary embodiment, mirror 22 is mounted onto a piezo-translation stage driven by a 10 Hz saw-tooth waveform with an amplitude of 50 μm. In various other embodiments, however, modulator 23 may be a phase-modulating device (e.g., electro-optic phase modulator or acoustic phase modulator) or another suitable device for introducing a suitable Doppler frequency modulation. In various embodiments, the optical path-length in the reference arm or in the sample arm may be modulated which has the same or similar effect as moving mirror 22 back and forth at a constant speed. In an embodiment, a method of stretching the optical fiber may be used.

In various embodiments, the modulation of the interferogram may also be provided by probe 26. In an exemplary embodiment, probe 26 may be configured such that the input signal is scanned with an offset reference to the pivot point.

The light returning from reference arm 14 and the light returning from sample arm 16 (the spectral signal) may be recombined and coupled into a single mode fiber by coupler 12 for introduction to a detection arm 30. As illustrated, detection arm 30 comprises a spectrometer 34 including one or more of various optics 36 including, but not limited to, one or more collimators, one or more diffracting/transmission gratings, and one or more lenses (not illustrated). In exemplary embodiments, optics 36 may include a 30-millimeter (mm) focal length collimator, a 1200 lines/mm diffracting grating, and an achromatic focusing lens with a 150 mm focal length. In various embodiments, spectrometer 34 may have a designed spectral resolution of, for example, 0.055 nm, resulting in an optical range of approximately 6.4 mm in air, i.e. the full depth in Fourier space where the positive frequency space (3.2 mm) may be used for micro-structural imaging and the negative frequency space (3.2 mm) for flow imaging. In an embodiment, the signal sensitivity of 95 dB may be measured at z=+0.5 mm and may be dropped to 80 dB at z=+2.0 mm when the camera integration time is set at 34.1 μs. Such parameters are exemplary and may be modified in a variety of ways in accordance with the embodiments of the present invention.

In embodiments employing a broadband light source, spectrometer 34 may include a detector such as a charge-coupled device (CCD) 38 configured to detect a spectral interference signal. CCD 38 may include one or more of a line scan camera and an area scan camera. An exemplary suitable CCD 38 may be a CCD consisting of 2048 pixels, each 10×10 μm in size and 10 bits in digital depth, and capable of a 29.2 kHz line rate. For those embodiments wherein light source 10 comprises a tunable laser rather than a broadband light source, however, OCT/OAG apparatus 100 may include a diffusion amplifier that may comprise one or more single element detectors rather than spectrometer 34. For example, one or more dual-balanced photo-diode detectors may be used.

As illustrated, reference arm 14, sample arm 16, and detection arm 30 include polarization controllers 18, 24, and 32, respectively. Polarization controllers 18, 24, 32 may be configured to fine-tune the polarization states of light in OCT/OAG apparatus 100. Although an OCT/OAG apparatus within the scope of the present invention may include more or less polarization controllers than illustrated, provision of polarization controllers 18, 24, and 32 in reference arm 14, sample arm 16, and detection arm 30, respectively, may advantageously maximize the spectral interference fringe contrast at CCD 38 (or another suitable detector).

In various embodiments, OCT/OAG apparatus 100 may include one or more user interfaces 40 for one or more purposes including displaying images, input of data, output of data, etc.

As noted above, OCT/OAG apparatus 100 may be configured to build a 3-D data volume set by scanning sample 28 with a sample light in x, y, and λ (z) directions to obtain a 3-D spectral interferogram data set. In exemplary embodiments, probe 26 may be scanned in the lateral direction (x direction) by an x-scanner and in the elevational direction (y direction) by a y-scanner. In various ones of these embodiments, the x-scanner may be driven by a 10 Hz saw-tooth waveform with an amplitude equivalent to 2.2 mm, and the y-scanner may be driven at 0.02 Hz with an amplitude of 2.2 mm. If, for example, CCD 38 is configured to capture a focused light spectrum of 2048 pixels (A-scan) and 1000 discrete points are measured in the x direction, a data matrix slice of 1000 by 2048 elements is formed in the x direction (B-scan). If, for example, 500 discrete points are measured in the y direction over 2.2 mm, a final data volume of 1000 by 500 by 2048 (x-y-z) voxels may be built, with each half of Fourier space comprising 1000 by 500 by 1024 voxels (C-scan).

Figure 5:
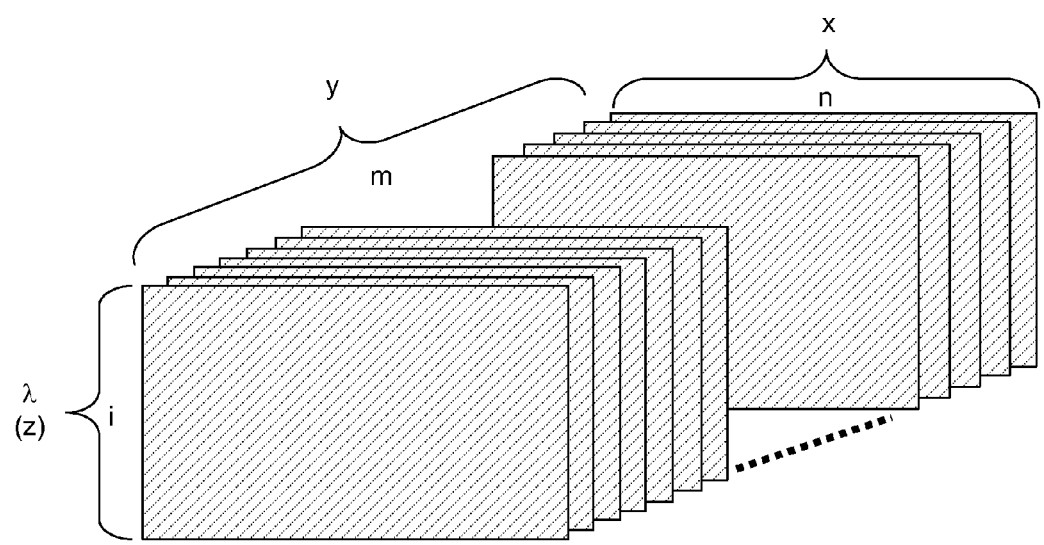
FIG. 5 illustrates a three-dimensional data cube/volume in accordance with various embodiments of the present invention.
Figure 6:
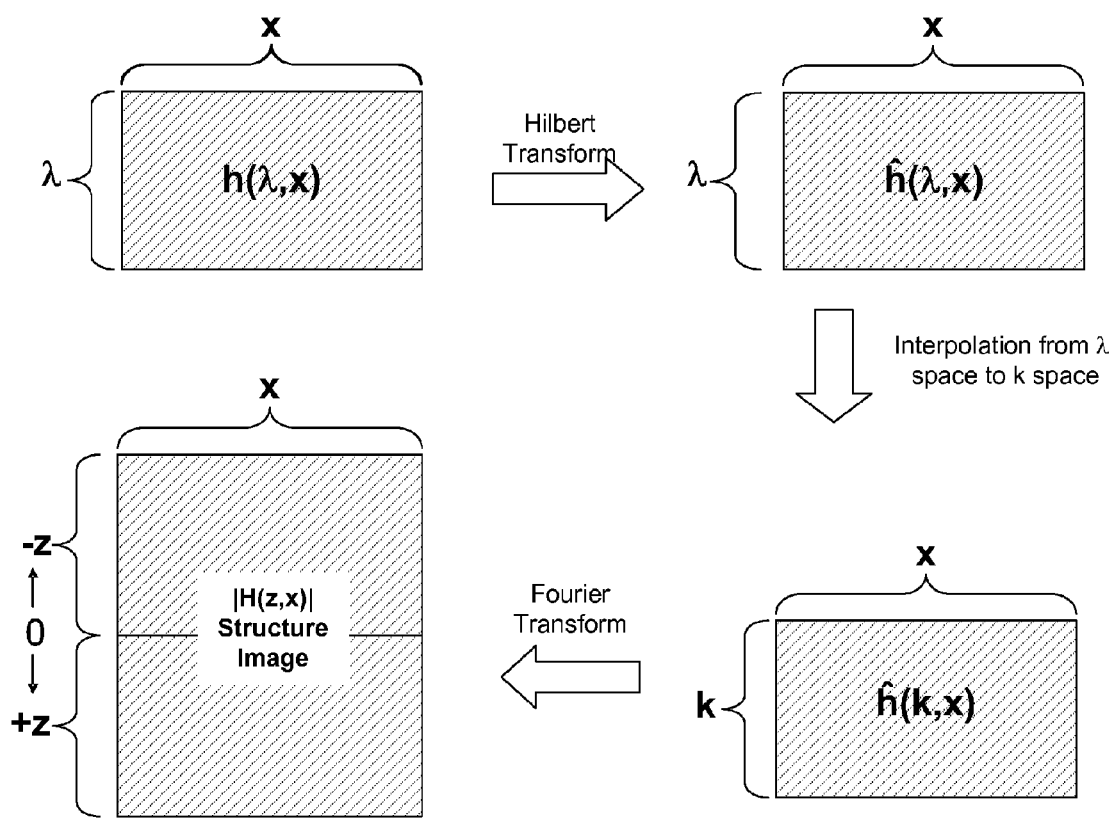
FIG. 6 illustrates an embodiment of an in vivo imaging method in accordance with various embodiments of the present invention.
Figure 7:
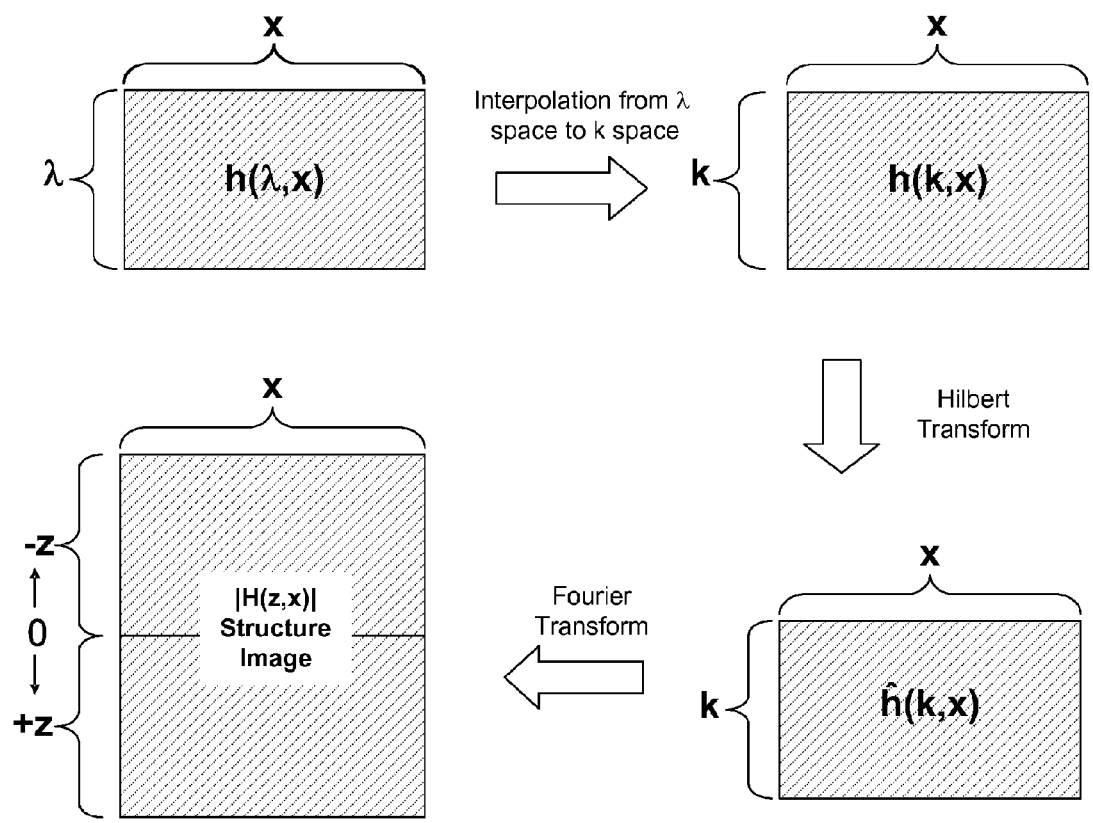
FIG. 7 illustrates another embodiment of an in vivo imaging method in accordance with various embodiments of the present invention.

Although scanning sample 28 in the x-y direction may be used to form a real-valued 3-D data volume, it is generally known that Fourier transformation of this real-valued data volume produces useful images in only half of Fourier space. Exemplary embodiments for producing a full range structural image are shown in FIG. 6 and FIG. 7, with reference to FIG. 5. FIG. 5 illustrates a 3-D data volume (cube) that may form part or all of a resulting image. As illustrated and in general convention, a scan in the λ direction may be referred to as an A-scan, and an A-scan may comprise a number, i, of pixels (or wavelength tuning steps in the case of a light source being a tunable laser source). A B-scan may comprise any number, n, of A-scans in the x direction. The series of 2-D data (e.g., a number, m, of B-scans) in the y direction may form the 3-D data cube, which may be referred to as a C-scan. As referred to herein, the x direction includes n columns and the λ direction includes i rows.

In various embodiments and as illustrated schematically in FIG. 6, raw cross-sectional data may be collected at the dimension of (x, λ) (i.e., h(λ,x)). An analytic function may be calculated on the real-valued cross-sectional data, row by row along the x dimension, to obtain a complex-valued function, $\hat{h}(\lambda,x)$, of the raw data. In various embodiments, the analytic function may be constructed by a Hilbert transform. In various embodiments, an un-distorted image may be obtained at least in part by interpolation of $\hat{h}(\lambda,x)$ from λ space to k space (i.e., the wave number space, $k=2\pi/\lambda$) to obtain $\hat{h}(k,x)$ along the λ dimension, column by column in the x dimension. In various ones of these embodiments, the interpolation may follow or precede calculation of the complex-valued function. FIG. 7 schematically illustrates an embodiment wherein interpolation precedes a complex-valued function calculation.

In various embodiments, a full range complex image (i.e., a cross-sectional x-z image), H(z,x), may be obtained by performing a Fourier transformation of $\hat{h}(k,x)$ along the k dimension, column by column in the x dimension. The full-Fourier space image may be obtained by taking the magnitude of H(z,x), (i.e., |H(z,x)|), which may result in doubling of usable depth, z (i.e., 2z), as illustrated in FIG. 6 (and FIG. 7).

In various embodiments, any one or more of the foregoing operations may be repeated for one or more h(λ,x) data sets available in the y dimension. A 3-D image may result from the one or more repetitions.

In various embodiments, a reference spectrum may be subtracted from the interferograms before the operations mentioned above so that the final image quality is enhanced. The reference spectrum may be obtained from ensemble-averaging of all the captured interferograms, i.e., averaging h(λ,x,y) along x or y directions.

In various embodiments, any one or more various operations may be performed first for the y dimension and then the x dimension, or vice versa. For example, in various embodiments, raw cross-sectional data may be collected at the dimension of (λ,y). An analytic function may then be calculated on the real-valued cross-sectional data, row by row along the y dimension, to obtain a complex-valued function, $\hat{h}(\lambda,y)$, of the raw data. In various embodiments, an un-distorted image may be obtained at least in part by interpolation of $\hat{h}(\lambda,y)$ from λ space to k space (i.e., the wave number space, $k=2\pi/\lambda$) to obtain $\hat{h}(k,y)$ along the λ dimension, column by column in the y dimension. In various ones of these embodiments, the interpolation may follow or precede calculation of the analytic function. A complex OCT image, H(z,y), may be obtained by performing a Fourier transformation of $\hat{h}(k,y)$ along the k dimension, column by column in the y dimension. The full-Fourier space OCT image may be obtained by taking the magnitude of H(z,y), (i.e., |H(z,y)|), which may result in doubling of usable depth, z (i.e., 2z). In various embodiments, any one or more of the foregoing operations may be repeated for one or more h(λ,y) data sets available in the x dimension. In various embodiments, a 3-D image may result from the one or more repetitions.

In vivo movement of material in a structure may be imaged in accordance with various embodiments of the present invention. For example, flow of blood, through blood vessels and otherwise, may be imaged. In various embodiments, indications of the direction of the flow may also be imaged. In general, imaging of non-stationary objects using any one or more of the previously-discussed methods may be affected by instantaneous phase changes (Doppler shift) which may cause energy leakage into a negative frequency plane (i.e., mirror plane). However, leakage generally is localized, i.e. only occurring at the site of movement (e.g., where there is blood flow). The other stationary object(s) may still be imaged according to one or more of the previously discussed methods.

Although not intended to limit the scope of embodiments of the present invention, the following general discussion may be helpful for understanding various mathematical and physical principles underlying some embodiments. According to various embodiments, a method for imaging movement in a tissue may include mapping velocities moving into the tissue away from the surface into one image and velocities moving out of the tissue toward the surface into a second image. Considering a real function that varies with two variables, both of time coordinates, $t_1$ and $t_2$ $$B(t_1,t_2)=\cos(2\pi f_0 t_1+2\pi(f_M-f_D)t_2+\phi) \quad \text{(Equation 1)}$$

where $f_0$, $f_M$ and $f_D$ are the frequency components, respectively and $\phi$ is a random phase term. For purposes of the discussion herein, $f_0$ and $f_M$ are assumed to be two modulation frequency components whereas $f_D$ is a Doppler frequency component. It may also be assumed that there is no correlation between $t_1$ and $t_2$, and when $t_1$ varies $t_2$ is constant and vice versa. The analytic function of Equation 1 against $t_2$ can be constructed through Hilbert transformation if the Bedrosian theorem holds, which states that the modulation frequency $f_M-f_D$ does not overlap the signal bandwidth caused by the random phase fluctuation term $\phi$. Under this condition, the Hilbert transform of Equation 1 is equal to its quadrature representation. Since the function $B(t_1,t_2)$ is modulated by the frequency $f_M-f_D$, and $2\pi f_0 t_1$ is a constant phase term, if $f_M-f_D>0$ the analytic function of Equation 1 can be written as:

$$\hat{H}(t_1,t_2)=\cos(2\pi(f_M-f_D)t_2+2\pi f_0 t_1+\phi)+ j\sin(2\pi(f_M-f_D)t_2+2\pi f_0 t_1+\phi) \quad \text{(Equation 2)}$$

where $j=\sqrt{-1}$; whereas if $f_M-f_D<0$, Equation 1 can be written as:

$$\hat{H}(t_1,t_2)=\cos(2\pi(f_M-f_D)t_2+2\pi f_0 t_1+\phi)- j\sin(2\pi(f_M-f_D)t_2+2\pi f_0 t_1+\phi) \quad \text{(Equation 3)}$$

From the mathematical point of view, Equation 3 is the complex conjugate of Equation 2. Performing the Fourier transformation against the time variable $t_1$ (note that $t_2$ is now constant), the frequency component $f_0$ of Equation 2 is placed in the positive space in the entire Fourier space, whereas the frequency component $f_0$ of Equation 3 is placed in the negative space. Accordingly, imaging of the movement of material in a structure is possible.

Referring again to the exemplary embodiment of an OCT/OAG apparatus 100 illustrated in FIG. 4, assuming that the reference mirror 22 mounted on the piezo-stage (modulator 23) moves at a velocity $\bar{v}_{ref}$, with the probe beam proceeding in the B-scan (x-scan) at a velocity of $v_x$ (scalar), and further assuming that a reflecting particle that is detected by OCT/OAG apparatus 100 also moves but with its directional velocity projecting onto the probe beam direction being $\bar{v}_s$, then for simplicity one can state the spectral interferogram in the wavelength $\lambda$ domain as:

$$B\left(\frac{1}{\lambda}, x\right) = \cos\left(\frac{4\pi\left(z_s + (\bar{v}_{ref} + \bar{v}_z)\frac{x}{v_x}\right)}{\lambda} + \varphi(x, z, \lambda)\right) \quad \text{(Equation 4)}$$

Note here that vector representations are used for velocities with the movement toward the incident beam being positive and the opposite being negative. The term $z_s$ is the initial depth-position of the reflecting particle (e.g., a red blood cell) at the lateral position x, and $\bar{v}_z$ is the velocity of the reflecting particle, such that the pathlength difference between sample arm 16 and reference arm 14 is $2(z_s+(\bar{v}_z+\bar{v}_{ref})t_x$, where $t_x=x/v_x$ is the scanning time of the probe beam in the B scan, and the factor of 2 accounts for the round trip of the sampling light scattered from the sample 28 back into the interferometer. The term $\phi(x,z,\lambda)$ is a random phase function that relates to the phases of the optical heterogeneous sample. The time $t_x=0$ would be the start of a B scan. Hence, $B(1/\lambda,x)$ is a sinusoidal oscillation function versus x for each $1/\lambda$ value. Accordingly, Equation 1 and Equation 4 would be identical if the following substitutions are used:

$$f_0 = z_s,\ t_1 = \frac{2}{\lambda},\ f_M = \frac{2\bar{v}_{ref}}{\lambda},\ f_D = -\frac{2\bar{v}_s}{\lambda},\ t_2 = t_x$$

Thus, the values of $\bar{v}_{ref}$ and $\bar{v}_s$ may determine whether the analytic function of Equation 4 constructed through the Hilbert transformation is turned into Equation 2 or Equation 3. The analytic function may be sequentially constructed through the Hilbert transformation to the B-scan along the x-axis at each $1/\lambda$. During the operation, the factor $4\pi z_s/\lambda$ may be a constant phase since it does not vary with x.

If $\bar{v}_s=0$, positive velocities ($\bar{v}_{ref}$) would modulate the signal with positive frequencies in x-space, and negative velocities with negative frequencies. The Hilbert transformation converts the information of the modulated signal versus x into a complex number $\hat{H}(1/\lambda,x)$, but now any subsequent Fast Fourier Transform (FFT) towards $2/\lambda$, $$FFT\left\{\hat{H}\left(\frac{1}{\lambda}, x\right)\right\}\bigg|_{\frac{2}{\lambda}},$$

of the Hilbert-encoded information would map positive frequency components into the positive-frequency space and map negative frequency components into the negative-frequency space of the FFT result, so that full range frequency space can be utilized for imaging. This is in contrast to simply taking $$FFT\left\{B\left(\frac{1}{\lambda}, x\right)\right\}\bigg|_{\frac{2}{\lambda}},$$

which would map both positive and negative frequencies into both the positive- and negative-frequency spaces of the transform, resulting in only half of the space being useful for imaging.

For a moving particle (e.g., a blood cell), $v_s \ne 0$. The particle movement may modify the modulation frequency through the velocity mixing, $\bar{v}_{ref}+\bar{v}_s$, similar to the frequency mixing in the signal processing discipline. An opposite movement of the particle relative to the movement of the reference mirror 22 may result in a decrease of the difference in photon pathlength between sample arm 16 and reference arm 14 and decreases the effective frequency of the modulation. If the value of $v_s$ is sufficiently large, the value $\bar{v}_{ref}+\bar{v}_s$ may change its sign. Consequently, after the operations of Hilbert and Fourier transforms, the corresponding signal due to the particle movement may map into the frequency space opposite to that with $v_s=0$. However, any small particle movement that is not strong enough to change the sign of the value may still map to the frequency space as that when $v_s=0$. Hence, the signals from the perfused blood cells and the bulk static tissue may be separated in the frequency space of FFT, with the background noise due to small tissue movements rejected in the space that represents the image of blood perfusion.

Figure 8:
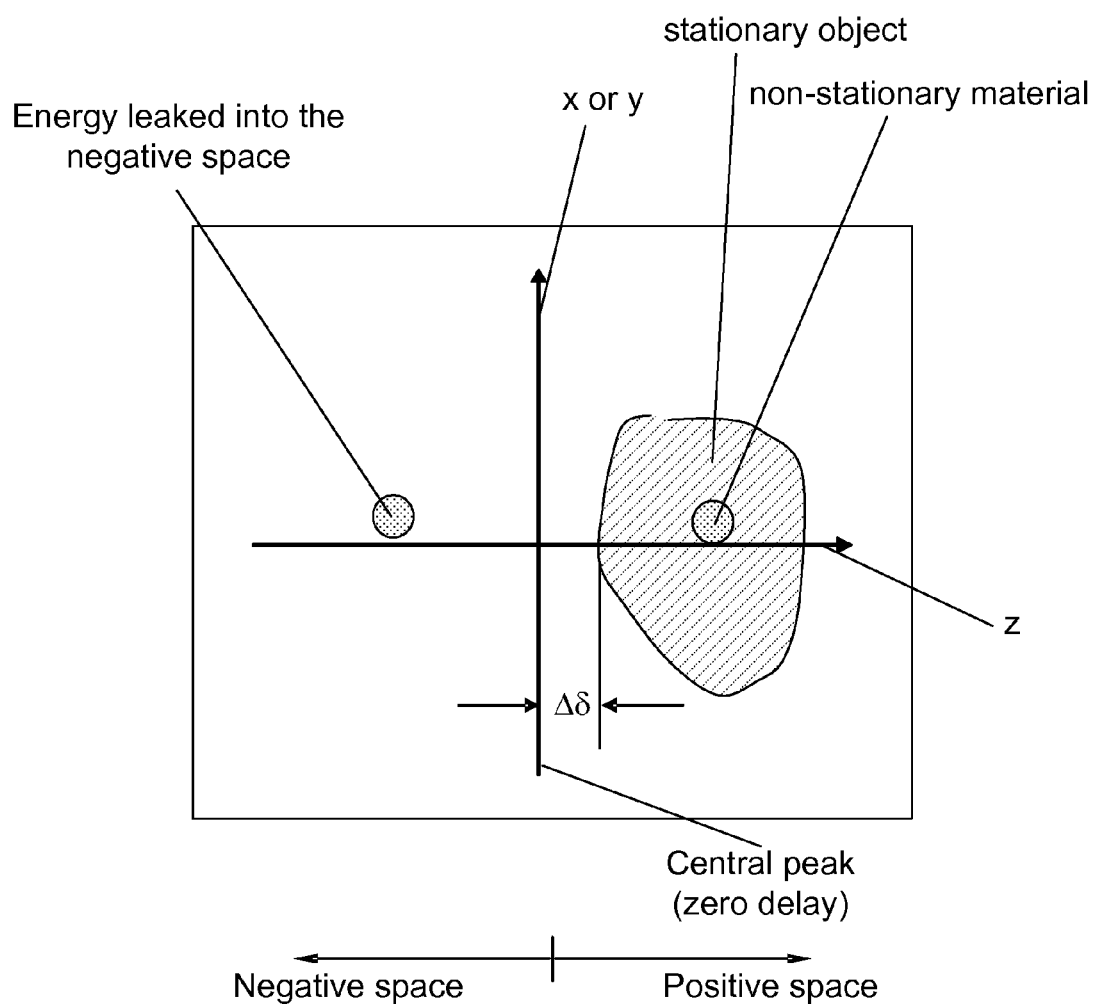
FIG. 8 illustrates an in vivo image in accordance with various embodiments of the present invention.
Figure 9:
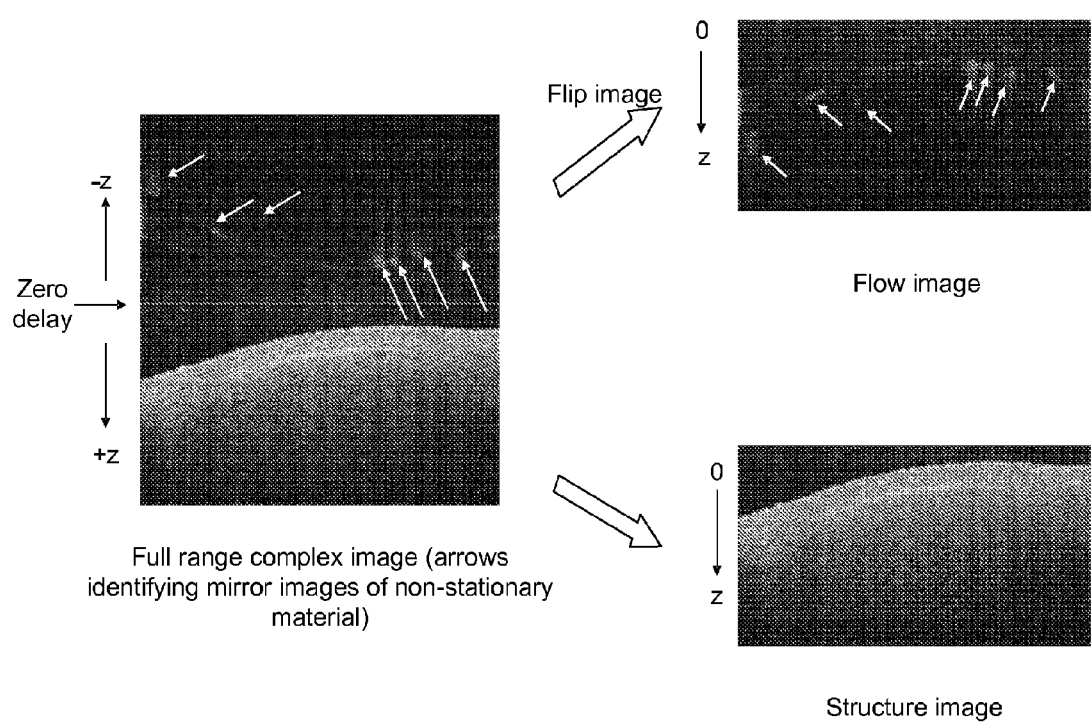
FIG. 9 illustrates an in vivo image in accordance with various embodiments of the present invention.

Accordingly, in various embodiments, leakage of energy into the negative frequency plane may be harnessed to image flow of material (or other movement of material) in real time in vivo. FIG. 8 and FIG. 9 illustrate embodiments of flow imaging (non-stationary material). Also shown are images of a structure (stationary object) in a positive area of Fourier space. In various embodiments and as shown, a structure image may be positioned substantially in a positive space and a flow image positioned substantially in the negative space, the flow image being a mirror image of its actual position relative to the structure. In various embodiments and as shown in FIG. 9, a combined structure/flow image may be separated into 2 or more images—e.g., a structure image and a flow image. For example, the positive space may represent a structure image and a flipped version of the negative space may represent a flow image.

In an exemplary embodiment of a method for imaging in vivo flow (or other movement of material), a sample is positioned a distance, $\Delta\delta$, away from the zero delay and in the positive space (as shown in FIG. 8). In various ones of these embodiments, positioning the sample away from the zero delay line may prevent or reduce the image of the stationary aspect of the sample from crossing over the zero delay and possibly resulting in overlapped images.

Figure 10:
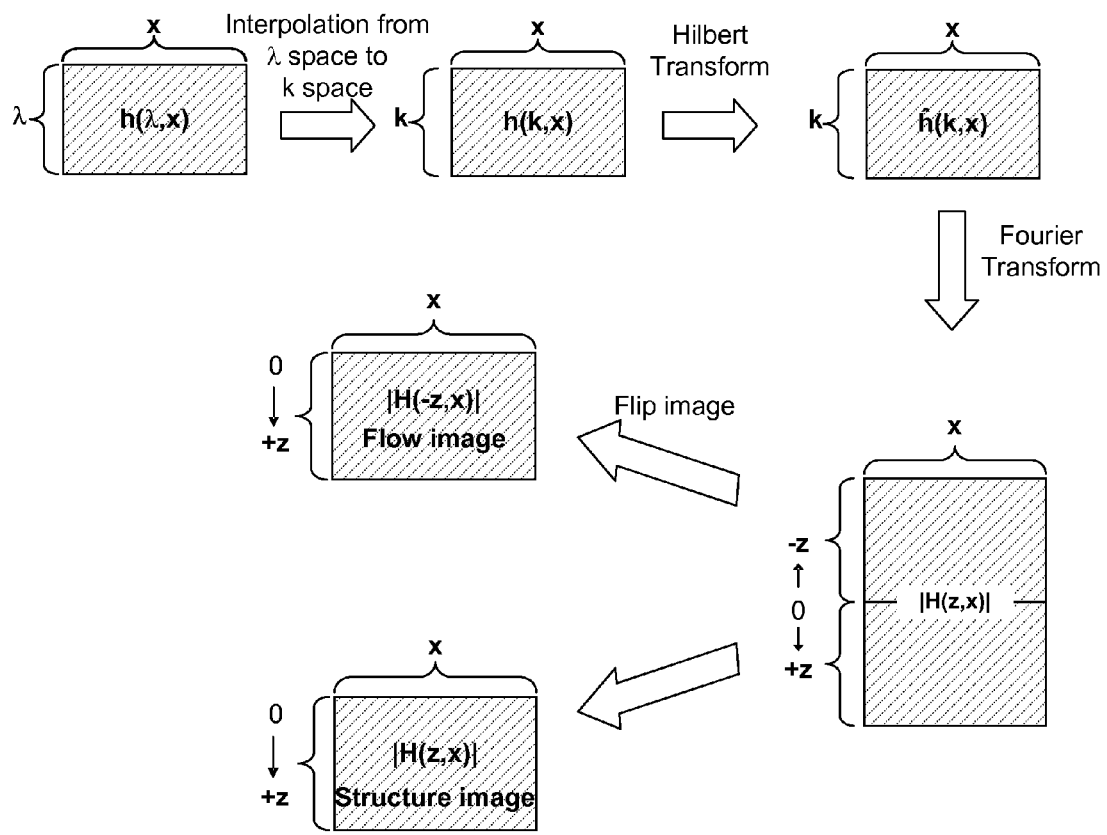
FIG. 10 illustrates another embodiment of an in vivo imaging method in accordance with various embodiments of the present invention.
Figure 11:
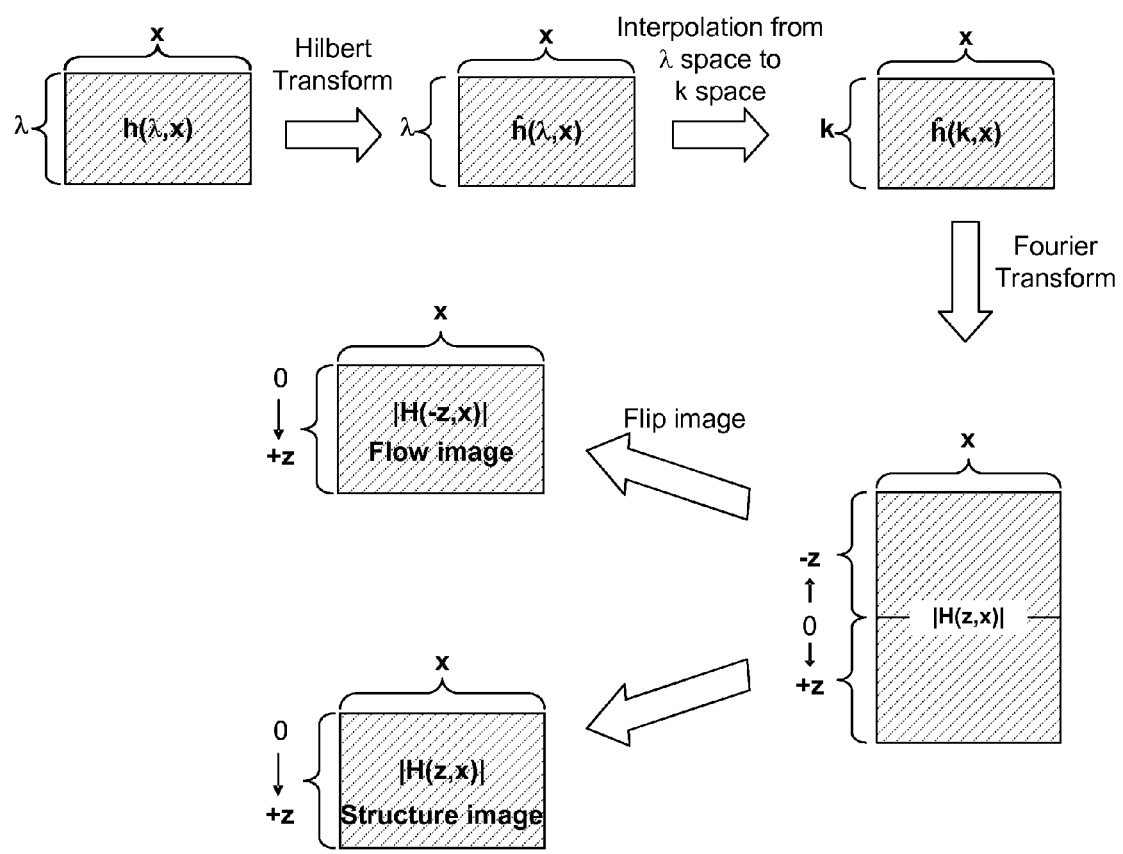
FIG. 11 illustrates another embodiment of an in vivo imaging method in accordance with various embodiments of the present invention.

In various embodiments and as shown in FIG. 10, raw cross-sectional data may be collected at the dimension of $(x,\lambda)$ (i.e., $h(\lambda,x)$). An analytic function may be calculated on the real-valued cross-sectional data, row by row along the x dimension, to obtain a complex-valued function, $\hat{h}(\lambda,x)$, of the raw data. In various embodiments, the analytic function may be obtained by a Hilbert transform calculation. In various embodiments, an un-distorted OCT image may be obtained at least in part by interpolation of $\hat{h}(\lambda,x)$ from $\lambda$ space to k space (i.e., the wave number space, $k=2\pi/\lambda$) to obtain $\hat{h}(k,x)$ along the $\lambda$ dimension, column by column in the x dimension. In various ones of these embodiments, the interpolation may follow or precede calculation of the complex-valued function. FIG. 11 illustrates an embodiment wherein interpolation precedes a complex-valued function calculation.

In various embodiments, a complex image (i.e., a cross-sectional x-z image), $H(z,x)$, may be obtained by performing a Fourier transformation of $\hat{h}(k,x)$ along the k dimension, column by column in the x dimension. A full-Fourier space image may be obtained by taking the magnitude of $H(z,x)$, (i.e., $|H(z,x)|$), which may result in doubling of usable depth, z (i.e., 2z), as shown in FIG. 10.

In an embodiment, $|H(z,x)|$ may be separated at the zero delay line (z=0) to form two images—a flow image and a structure image. In the illustrated embodiment, the flow image is formed in the negative space (i.e., z<0) and the structure image is formed in the positive space (i.e., z>0). In an embodiment, since the flow image may be a mirror image of its actual position relative to the structure image, the flow image may be flipped to obtain the true flow image (now z>0).

In various embodiments, any one or more of the foregoing operations may be repeated for one or more $h(\lambda,x)$ data sets available in the y dimension. A 3-D structural image and a flow image may result from one or more of the repetitions.

In various embodiments, the y dimension may be processed prior to processing the x dimension. For example, in various embodiments, raw cross-sectional data may be collected at the dimension of $(\lambda,y)$. An analytic function may then be calculated on the real-valued cross-sectional data, row by row along the y dimension, to obtain a complex-valued function, $\hat{h}(\lambda,y)$, of the raw data. In various embodiments, an un-distorted image may be obtained at least in part by interpolation of $\hat{h}(\lambda,y)$ from $\lambda$ space to k space (i.e., the wave number space, $k=2\pi/\lambda$) to obtain $\hat{h}(k,y)$ along the $\lambda$ dimension, column by column in the y dimension. In various ones of these embodiments, the interpolation may follow or precede calculation of the complex-valued function. A complex image, $H(z,y)$, may be obtained by performing a Fourier transformation of $\hat{h}(k,y)$ along the k dimension, column by column in the y dimension. The full-Fourier space image may be obtained by taking the magnitude of $H(z,y)$, (i.e., $|H(z,y)|$), which may result in doubling of usable depth, z (i.e., 2z). In various embodiments, any one or more of the foregoing operations may be repeated for one or more $h(\lambda,y)$ data sets available in the x dimension.

In embodiments wherein flow and structure images are obtained, the images may be fused or otherwise combined to provide a complete view of how blood (or other moving material) may be oriented within the structural tissue (e.g., blood moving through a vascular network). Using various embodiments of methods previously discussed, a flow image in negative space may be formed, flipped, and fused with a structure image to form a single angiographic image. The single image may allow for precise localization of moving components within tissue. In various embodiments, multiple of such images may be "mosaiced" to form a larger image.

Figure 12A:
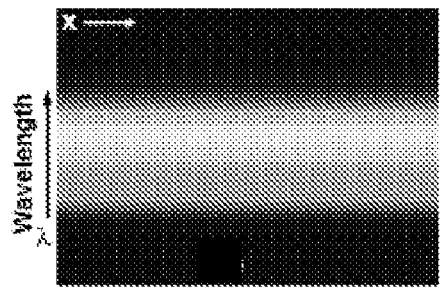
FIG. 12A illustrates a B scan of a mouse brain obtained using imaging methods in accordance with various embodiments of the present invention.
Figure 12B:
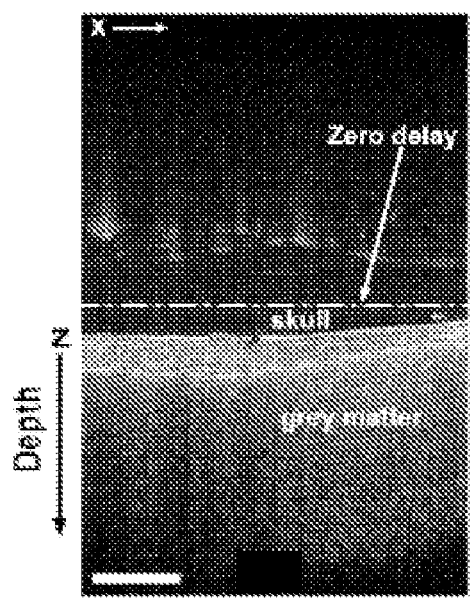
FIG. 12B illustrates the imaging result of FIG. 12A separated by the zero delay line into two equal spaces, the structure information in the bottom region and the flow information in the top region.
Figure 12C:
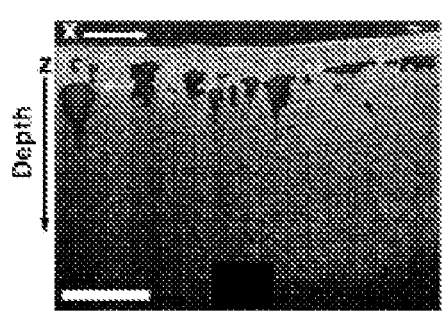
FIG. 12C illustrates the images of FIG. 12B with the top region folded and fused with the bottom region to produce an angiographic image including structure and flow information for the mouse brain.

In an embodiment, to validate that the OCT/OAG system can assess microvascular flow, a series of in vivo experiments to obtain transcranial images of the cerebro-vascular circulation of mice, with the cranium intact, were performed. The experimental protocol was in compliance with the Federal guidelines for care and handling of small rodents and approved by the Institutional Animal Care and Use Committee. A mouse was anesthetized and then the skin on the head was removed to create a window for OCT imaging through the cranium. The in vivo results are given in FIG. 12A-12C, where FIG. 12A depicts the data set representing a B scan containing a 2-D real-valued spectral interferogram in x-$\lambda$ (2.2 mm by 112 mm centered at 842 nm), and FIG. 12B shows the image obtained from the raw spectral interferograms of FIG. 12A representing one slice within the 3-D data set, wherein the entire Fourier space is separated into two equal regions. The bottom region is the positive frequency space including the cross-sectional structure information of the mouse cranium and cortex, but the blood vessels are difficult to identify. On the other hand, the top region is the negative frequency space in which the moving components (e.g., the red blood cells) can be seen. As the positive and negative frequency spaces are exactly mirrored, they can be folded to fuse a single image to localize with high precision the blood vessels within the structural tissue, as can be seen in FIG. 12C. The cortical structures and blood perfusion can be resolved at depths of about 1.5 mm through the cranium, a penetration depth that cannot be achieved with confocal microscopy. This depth may be extended further if a light source having a wavelength longer than 842 nm is used. The axial resolution for resolving blood vessel dimensions may be determined by the bandwidth of the light source used. In the subject experiment, the axial resolution was approximately 6 μm within the biological tissue, which is capable of resolving the capillaries that are of an average size of about 10 μm, and lateral resolution was approximately 16 μm which is determined by the objective lens that focused the light into the tissue.

Figure 13A:
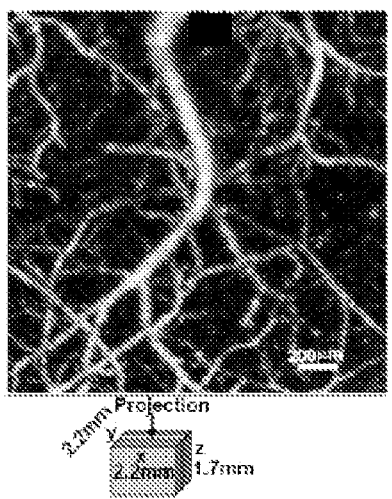
FIG. 13A illustrates a 2-D x-y projection view of cerebrovascular flow within a scanned volume of a mouse brain.
Figure 13B:
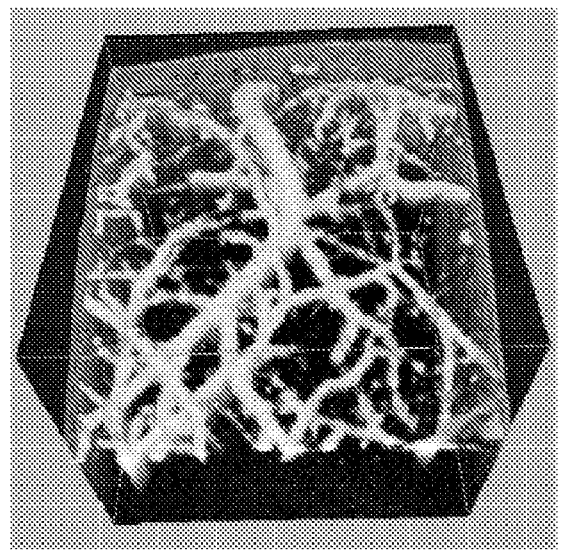
FIG. 13B illustrates a complete 3-D view of the mouse brain of FIG. 13A.

As discussed herein, 3-D imaging may be performed by evaluating spectral interferogram data slice (B scan) by slice, then re-combining to yield the 3-D volume data set (x-y-z), from which high quality information regarding vasculature, blood flow, and microstructures can be extracted. As shown in FIG. 13A, detailed 2-D vasculature mapping is obtained by projecting the 3-D flow image from the negative space into the x-y plane. The localized moving scattering elements in the negative space can be folded to combine with the 3-D structural image to provide a complete view of how the blood vessels are oriented in the structural tissue, as shown in FIG. 13B. In the embodiments illustrated in FIGS. 13A and 13B, the imaging speed was 10 frames/second and the entire image acquisition time was about 50 seconds. The imaging time may be decreased by employing a higher power light source and a higher speed of modulator (e.g., the piezo-translation stage). The computation time for post processing of images was approximately 4.2 seconds per slice on a conventional personal computing device, for a total of about 35 minutes for a full 3-D image.

Visualization of cerebro-vascular perfusion in 3-D in accordance with various embodiments of the present invention combined with quantification of blood flow may be desirable for investigating neurological diseases in small animal models. For example, ischematic thrombotic stroke is widely studied in small animal models such as a genetically-altered mouse. Accordingly, a detailed view of cerebro-vascular blood flow phenomena and regulation across the entire cerebral cortex at the level of individual blood vessels down to the capillaries may be important to better understand the pathophysiology of cerebro-vascular diseases and the potential benefits of pharmacological interventions. To illustrate the importance of embodiments of the present invention, multiple 3-D images of a mouse brain were collected over different regions of the skull, as illustrated in FIGS. 14A-14D. FIG. 14A shows the blood flow in the cerebral cortex of a mouse with the skull intact. Occlusion of one carotid artery does not cause cerebral infarction or neurological deficits in the mouse. FIG. 14B shows the same mouse while the right carotid artery was blocked for 5 minutes. As can be seen, it is apparent that the blood flow in the cortex is reduced as compared to the image in FIG. 14A, rather than in the right hemisphere only, which is consistent with known behavior. The capability of embodiments within the scope of the present invention to achieve such high resolution imaging of the cerebral cortex within minutes and without the need for dye injections, contrast agents, or surgical craniotomy illustrates its value in understanding the hemodynamics of the brain and other vascular networks. FIG. 14C illustrates the mouse brain with the skin folded aside and FIG. 14D illustrates the mouse brain with the skull removed for comparison to the imaged results.

Figures 15A, 15B:
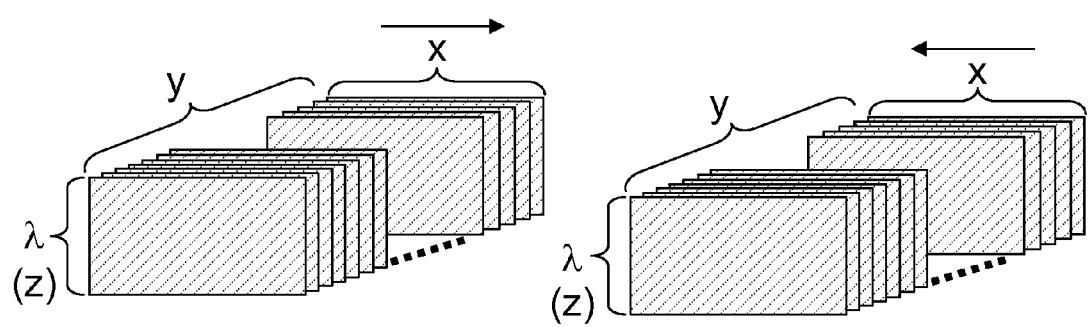
FIGS. 15A and 15B illustrate two 3-D data cubes obtained as a result of an imaging method in accordance with various embodiments of the present invention.

As noted herein, an indication of the direction of flow of material may be imaged in accordance with various embodiments. In an embodiment, 3-D OCT is provided as a method of imaging localized blood perfusion at the capillary level within microcirculatory beds, whose contrast is based on the endogenous scattering signals from moving blood cells. An embodiment of the present invention utilizes OCT for directional blood perfusion mapping in vivo. Such an embodiment may be achieved, for example, by linear translation of a reference mirror located in a reference arm (i.e., back and forth movement), synchronized with OCT cross-sectional (B) scans when 3-D imaging is performed. In an embodiment, a collection of all the B scans when the reference mirror moves toward the incident beam gives the blood perfusion that flows away from the incident beam direction, and vice versa. Therefore, two 3-D data cubes are obtained (FIGS. 15A and 15B). One is used to calculate the flow toward the probe beam direction (FIG. 15A), and the other is used to calculate the flow that is flowing away from the probe beam (FIG. 15B). An embodiment of the present invention also provides the ability to quantitatively assess blood perfusion.

In embodiments, it is desirable that the directional flow be imaged and visualized for a number of engineering and medical fields, for example in the study of complex flow dynamics in microfluidic mixers, and in the investigation of neurological phenomena for understanding mechanisms and therapeutic interventions in cerebro-vascular diseases, including ischemia, hemorrhage, vascular dementia, traumatic brain injury and seizure disorders.

Embodiments of the present invention provide multiple approaches to directional flow imaging, including hardware approaches and digital approaches, as discussed in further detail below, with reference to FIG. 4.

In an embodiment, directional flow mapping may be achieved by mounting reference mirror 22 onto a modulator 23 such as, for example, a piezo-translation stage. In an embodiment, such a stage may be driven by a 10 Hz triangle waveform. For the experiments described below, unless otherwise stated, the maximum magnitude of the linear translation given to mirror 22 is 21 µm. This introduces a constant modulation frequency of 1.0 kHz coupled into the interferograms captured by CCD camera 38 at the ascending curve of the triangle waveform, i.e. when mirror 22 is moved toward the incident reference beam direction, while it is −1.0 kHz otherwise. The probe beam was scanned in the lateral direction (x axis shown in FIGS. 15A and 15B) by the X-scanner, also driven by a 10 Hz triangle waveform with an amplitude equivalent to 2.2 mm, which may be synchronized with the waveform used to drive mirror 22. The Y-scanner, driven at a 0.02 Hz saw-tooth waveform with amplitude of 2.2 mm, scanned the probe beam in the elevational direction (y axis). In this manner, a 3-D data cube of the spectral interferograms, having 1000 by 500 by 2048 (x, y,λ) voxels, was collected by scanning the probe beam through the X-Y scanners. In such an embodiment using the arrangement described above, with the camera integration time set at 100 µs, it took 50 seconds to obtain such a volume data cube, from which the 3-D directional flow mapping was calculated. The collection of all the B scans when mirror 22 moves toward the reference beam gives the volume data set that may be processed to obtain the flow image that represents the particles, such as blood cells moving along with the incident beam direction, and the opposite flow image may be obtained from the data cube collected from the B scans when mirror 22 moves in the backward/reverse direction. The final exemplary volume image was 500 by 500 by 1024 voxels, representing a physical dimension of 2.2 by 2.2 by 2.4 mm (x,y,z) of the sample. An average refractive index of 1.35 for the tissue sample was used to scale the dimension in the z direction. In an embodiment, due to limited computer memory availability, the volume image may be cropped to remove the regions that do not contain useful information for imaging. The actions for probe scanning, piezo-stage translation, data acquisition, data storage and hand-shaking between them may be controlled by a custom software package, such as software written in Labview® language.

Efficient separation of the moving scatters from the static components in OCT/OAG relies on the motion-induced Doppler frequency that turns the Hilbert transformed analytic function of the spectral interferogram into its complex conjugate form for the signals resulting from the moving scattering elements. Thus, in the results presented herein, because the modulation frequency is ±1.0 kHz, if the Doppler frequency induced by the moving scatter is larger than 1.0 kHz in the opposite direction of the modulation frequency, the light scattering signals from the moving components appear in the negative space of the output Fourier plane, while the signals pertinent to the static scattering elements remain in the positive space, i.e. microstructural image equivalent to the conventional OCT image. In an embodiment, this imposes a minimum velocity of moving scatters that may be sensed by OCT/OAG, which may be determined by $$\pm v_{min} = \mp f_M \bar{\lambda}/(2\cos(\beta)) \quad \text{(Equation 5)}$$

where $\bar{\lambda}$ is the mean wavelength of the light source used, $\beta$ is the angle between the probe-beam and the flow velocity vector, and the sign "±" denotes the direction of the variables relative to the incident probe beam direction. For an exemplary system discussed herein, $v_{min}$ was estimated at ~0.42 mm/second in both directions. The normal velocity for red blood cells traveling in the arteriole, venule and capillary bed varies from approximately 0.5 to several tens of mm/s, thus the majority of perfused blood vessels may be detected by the described OAG system arrangement.

While blood vessels and imaging of blood perfusion are discussed extensively herein, embodiments of the present invention are not limited to imaging in such environments, and may be utilized in medical and non-medical situations to image directional flows.

Figures 16A, 16B:
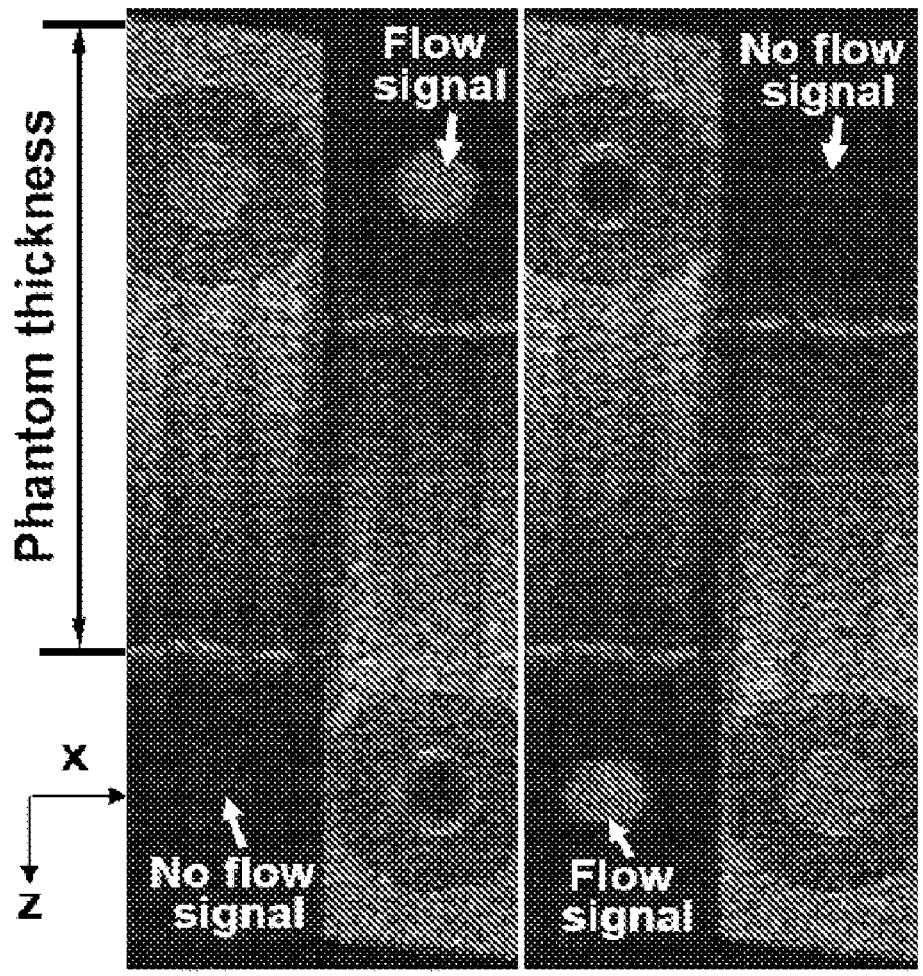
FIGS. 16A and 16B illustrate the results of experiments using a phantom in accordance with various embodiments of the present invention.

In an embodiment, to validate that the OCT/OAG system can measure bi-directional flow, a series of in vivo experiments using a flow phantom were performed. The phantom was made from gelatin mixed with 2% milk to simulate the static scattering elements in which a capillary tube with an inner diameter of ~250 µm was submerged and a 2% $TiO_2$ particle solution was flowing within it with a volumetric flow rate set at ~2.19 $mm^3$/minute. The angle between the probe beam and the tube was ~70°. Assuming the flow was laminar, the maximum velocity in the center of the tube projected onto the probe beam would be ~0.5 mm/second. To measure this flow, ~500 Hz modulation frequency was introduced into the spectral interferograms over the B scan by driving the reference mirror with a 10 Hz triangular waveform. This means that $f_M$=+500 Hz when the reference mirror moves toward the reference beam (ascending curve), and $f_M$=−500 Hz otherwise (descending curve). FIGS. 16A and 16B illustrate the imaging results from the measurements for such a flow phantom. In obtaining FIGS. 16A and 16B, 1000 A scans were continuously captured during a full cycle of a triangular wave form, with the first 500 A scans from the descending curve and the rest from the ascending curve. These 1000 A scans were saved as a single B scan for further data processing to obtain the image. Therefore, in accordance with an embodiment, the first and the second halves of the final image represent the images that may be obtained from the data captured when the reference mirror is moved in the backward and forward directions, separately. Furthermore, in an embodiment in accordance with the theoretical framework, these two halves of the image should be symmetrical to each other relative to the zero-delay line. This is confirmed from FIGS. 16A and 16B. FIG. 16A was obtained when the scattering fluid in the tube flowed upwards (i.e. the projection of flow direction on the optical axis was against the probe beam incident direction). Thus, the flow signal may only be seen in the flow imaging plane of the second half of the image (i.e. in the upper left quadrant). Next, the flow in the capillary tube was reversed, and the imaging resulted in FIG. 16B. Thus, in an embodiment, and as made clear by these experiments, OCT/OAG imaging is directionally sensitive. The size of flow signals in this case was about 65% of the tube cross-section area, implying that the flow velocities of more than 0.2 mm/second (assuming the laminar flow in the tube) were detected by the system and agreed well with the prediction of Equation 5. These experiments also confirmed that, in an embodiment, the full output plane of Fourier space may be used for imaging purposes because the mirror image of the static components is eliminated in the imaging.

Figure 17:
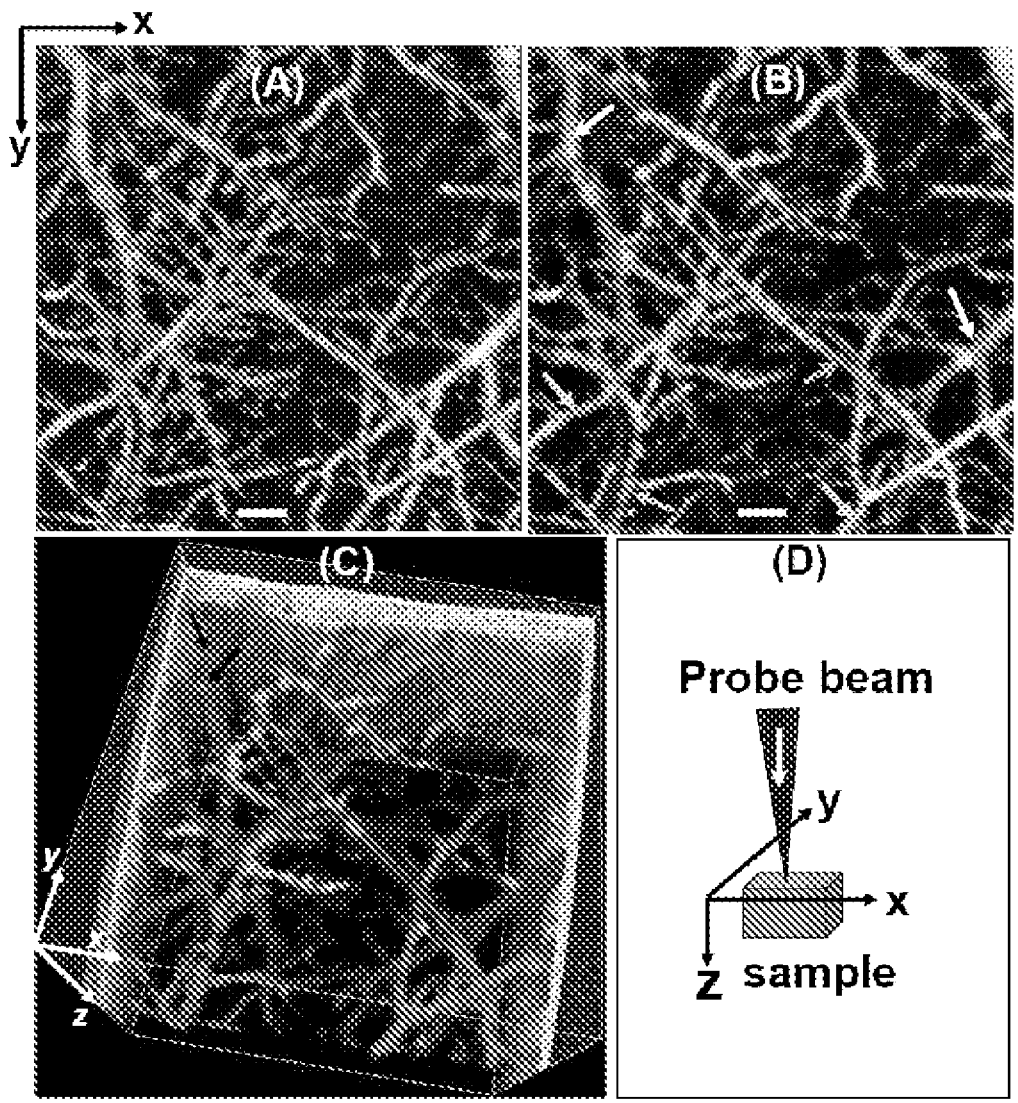
FIG. 17 (panels A, B, C, and D) illustrate a micro-vascular flow map obtained from optical angiography imaging of a mouse brain in vivo with the cranium intact in accordance with various embodiments of the present invention.

In accordance with an embodiment, an experiment was conducted to image the directional micro-vascular blood flow over the brain cortex in a live mouse with the cranium intact. The experimental protocol was in compliance with the Federal guidelines for care and handling of small rodents and approved by the Institutional Animal Care and Use Committee. The mouse was anesthetized and then the skin on the head was removed to create a window for OAG imaging through the skull bone. The in vivo results are given in FIG. 17 (panels A, B, C, and D), where FIG. 17A provides the x-y projection image of vascular flow map without directional information, and FIG. 17B illustrates the directional blood flow map fused from the two projection images obtained when the reference mirror moved forward and backward, separately, where the arterioles and venules may be identified. More importantly, with the directional flow map, one would have an opportunity to assess the flow dynamics within vessels in more detail, particularly the micro-flow turbulence in the vessel bifurcations. FIG. 17C provides a 3-D volume rendered bi-directional flow image together with micro-structural images (bounded on the three sides as shown) that may be used to infer the flow directions in 3-D space with the coordinate definition given in FIG. 17D.

Although extremely encouraging, the direction of flow sensed by OAG depends strongly on the 3-D geometry of the vascular network relative to the OAG probe beam direction, and this dependence complicates the interpretation of blood perfusion (see FIG. 17B and FIG. 17C). This complication however occurs in all the measurement techniques that are based on the Doppler principle, including Doppler OCT. The ability to image the direction of blood flow down to the capillary level is important in the investigation of a number of diseases, including neuropathology and tumor angiogenesis, and is provided in accordance with embodiments of the present invention despite the potential limitations identified herein.

In an embodiment, the system sensitivity of OAG to image directional flows may be very high, close to a zero flow velocity. In a practical sense, the lower limit of flow imaging may be determined by the bandwidth of spectral interference signals that result from the lateral scanning of the probe beam due to the optical heterogeneity of the biological tissue. The bandwidth of a spectral interference signal may be determined by the probe beam sampling width when it scans over a sample. The efficient separation between the signals from the static and moving elements also requires that the modulation frequency and the signal bandwidth are not overlapped. Thus, in an embodiment, the minimum blood flow velocity that may be practically detected by the OAG system is half of the spectral interference signal bandwidth. The interference signal bandwidth was typically ~800 Hz in the performed in vivo animal experiments with the system configurations described in FIG. 4. In an embodiment, with such a bandwidth, the minimum flow velocity for such an OAG system is ~170 µm/second for in vivo imaging. However, such sensitivity is well capable of imaging blood cells traveling single file, e.g., in the smallest unit of blood vessels, the capillaries.

In an alternative embodiment of the invention making use of a digital imaging approach, the mirror discussed above does not need to move. Thus in an embodiment, mirror 22 in FIG. 4 may be stationary while 3-D imaging is performed. In an embodiment, the essence of such a digital approach is a method to process the 3-D data volume to produce the directional and quantitative flow imaging. For clarity, the use of 2-D images to produce the resulting 2-D image is discussed here. The description also applies to the 3-D case.

In an embodiment, only one 3-D data cube as shown in FIG. 15 is collected within which the spectral interference signals captured by the detector arm 30 may or may not be modulated. By use of signal processing techniques and the real value property of the interference signal, this 3-D data cube may be modulated digitally and processed to produce both the structural and directional flow images of the sample.

Figure 18:
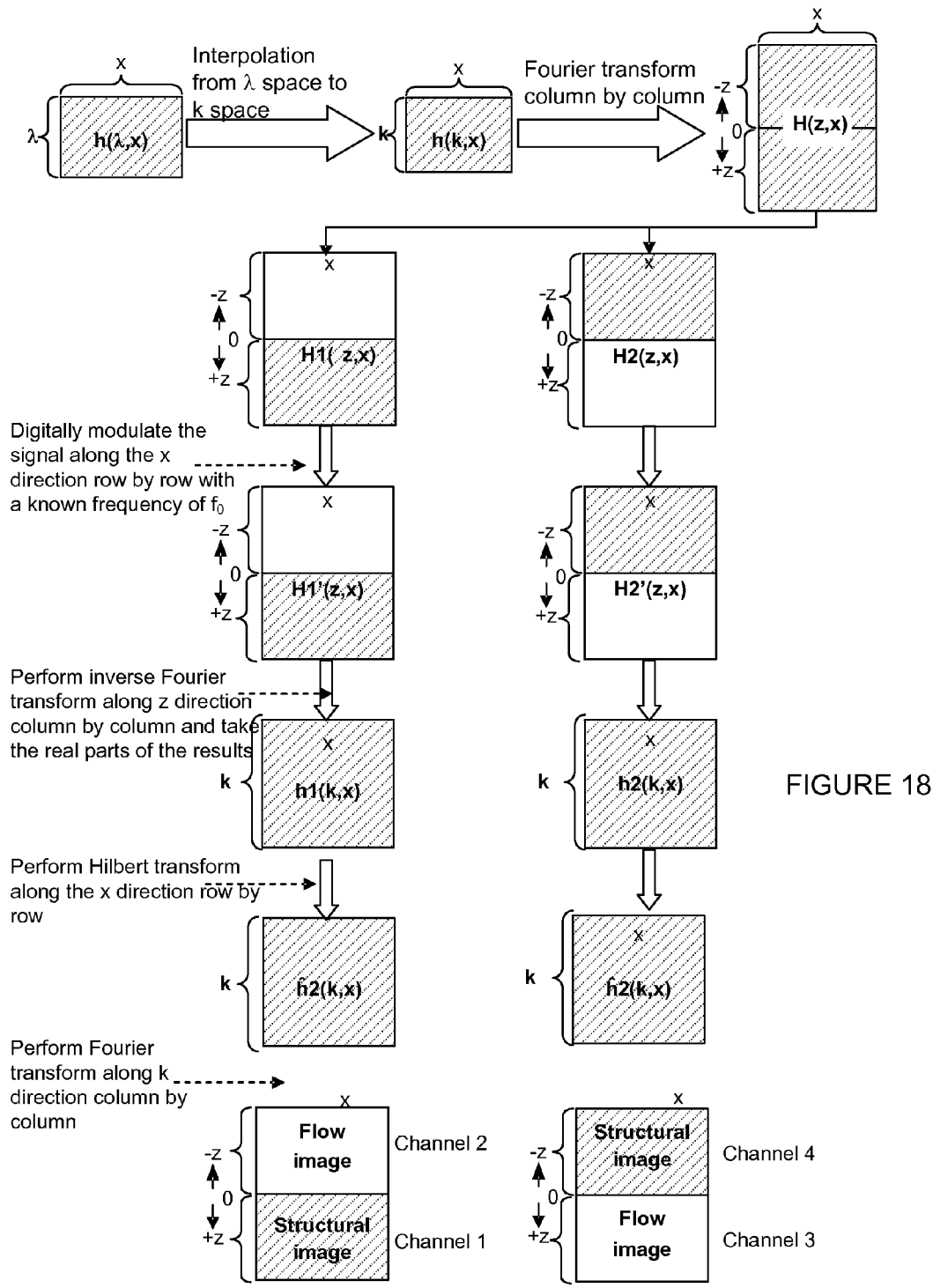
FIG. 18 illustrates a digital approach for directional flow mapping in accordance with various embodiments of the present invention.

Exemplary steps for performing a digital method in accordance with an embodiment of the invention are provided below. In an embodiment (see FIG. 18), take one cross-sectional data point at the dimension of $(x,\lambda)$, $h(\lambda,x)$, at any one time. Perform the interpolation for $h(\lambda,x)$ from $\lambda$ space to k space along the $\lambda$ dimension column by column to obtain $h(k,x)$. Calculate the Fourier transform column by column along the $\lambda$ dimension, resulting in $H(z,x)$ that possesses the positive and negative spaces in z. Form two functions from $H(z,x)$: forcing the negative space of $H(z,x)$ equal to zero to form $H1(z,x)$, and forcing the positive space of $H(z,x)$ equal to zero to form $H2(z,x)$. Modulate $H1(z,x)$ and $H2(z,x)$ digitally with a known frequency of $f_0$ along the x dimension to obtain the modulated signals $H1'(z,x)$ and $H2'(z,x)$. In an embodiment, $f_0$ is equivalent to the mirror moving in the hardware approach with relation of $f_0=2v/\lambda$, where v is the moving speed of the mirror. Perform the inverse Fourier transformation to $H1'(z,x)$ and $H2'(z,x)$ along the z dimension and then take only the real parts or imaginary parts of the results that form $h1(k,x)$ and $h2(k,x)$. Calculate the analytic function (for example Hilbert transform) along the x dimension row by row in the $\lambda$ dimension to obtain the complex valued function of the data in the previous operation. This operation results in $\hat{h}1(k,x)$ and $\hat{h}2(k,x)$. Perform a Fourier transformation of $\hat{h}1(k,x)$ and $\hat{h}2(k,x)$ along the k dimension to obtain the complex OCT images, $H1(z,x)$ and $H2(z,x)$ and take the magnitudes of the results. Separate $|H1(z,x)|$ and $|H2(z,x)|$ at the zero delay line (z=0) to form four images (four channels in FIG. 18). Channel 1 and Channel 4 are the images that represent the structural image of the sample. Channel 2 represents the flow image that indicates the flow moving toward the incident probe beam. Channel 3 represents the flow image that indicates the flow moving away from the incident probe beam.

In an embodiment, the process outlined above may be repeated for each $h(\lambda,x)$ data set available in the y direction in the 3-D data cube. As a result, in an embodiment, both the 3-D structural and directional flow images may be obtained.

In various embodiments, any one or more various operations may be performed first for the y dimension and then the x dimension, or vice versa.

In an embodiment, the modulation frequency $f_0$ is equivalent to the mirror moving in the hardware approach with a relationship of $f_0=2v/\lambda$, where v is the moving speed of the mirror. Therefore, quantitative flow imaging may be performed by progressively changing the modulation frequency $f_0$. In this way, any flow velocity values may be determined.

While the operations identified above are presented in an ordered manner, in embodiments, there is no specific order in performing the various operations. In an embodiment, one may modify the order of operations while still obtaining the same or similar results.

In an embodiment, another qualitative and quantitative flow imaging method uses a filtering technique with a specific frequency band centered at a frequency f between performing the inverse Fourier transformation and calculating the analytic function. The frequency f corresponds to a particular value of the flow velocity. In embodiments, the filtering technique that may be used includes a rectangle function, Gaussian function, or specifically designed filter function that is often encountered in the signal processing discipline.

Figure 19:
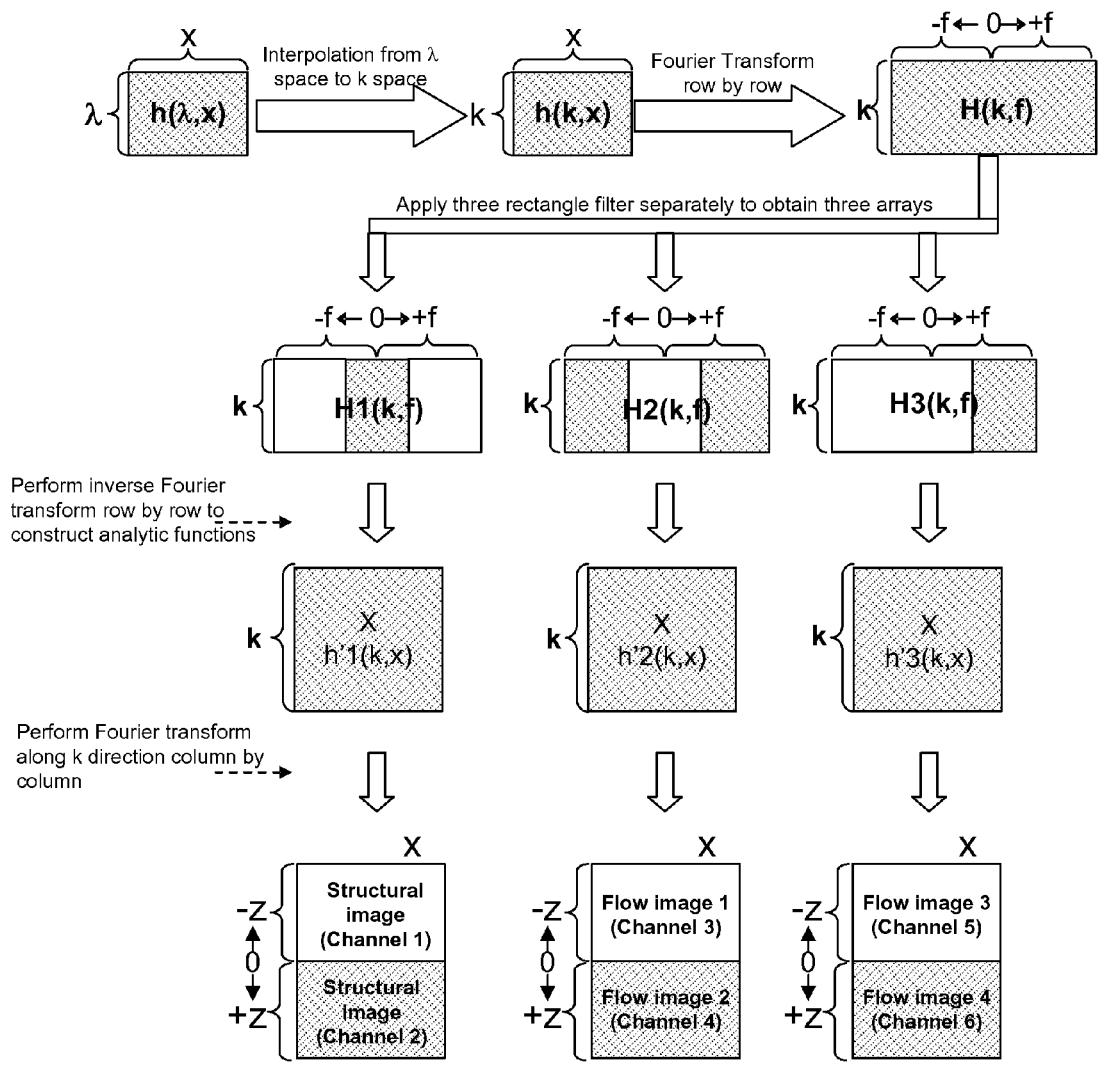
FIG. 19 schematically illustrates an embodiment of a digital filtering method for directional flow mapping in accordance with various embodiments of the present invention.

An exemplary embodiment of a digital filtering method for directional flow mapping is schematically illustrated in FIG. 19. In the embodiment, a cross-sectional data point may be taken at the dimension of $(x,\lambda)$, $h(\lambda,x)$, at any one time. An interpolation may be performed for $h(\lambda,x)$ from $\lambda$ space to k space along the $\lambda$ dimension column by column to obtain $h(k,x)$. The Fourier transform may be calculated row by row along the x dimension, resulting in $H(k,f)$ having the positive and negative frequency spaces in f.

Three functions may be formed from $H(k,f)$: multiplying a first rectangle function $t1(k,f)$ to form $H1(k,f)$; multiplying a second rectangle function $t2(k,f)$ to form $H2(k,f)$; and multiplying a third rectangle function $t3(k,f)$ to form $H3(k,f)$. The analytic functions may be calculated (e.g., by using inverse Fourier transform) along the f dimension row by row in the k dimension to obtain the complex valued function of the data in the previous operation. This operation may result in $\hat{h}1(k,x)$, $\hat{h}2(k,x)$ and $\hat{h}3(k,x)$.

In various embodiments, a Fourier transformation of $\hat{h}1(k,x)$, $\hat{h}2(k,x)$, and $\hat{h}3(k,x)$ may be performed along the k dimension to obtain the complex OCT images, $H1(z,x)$, $H2(z,x)$, and $H3(z,x)$. The magnitudes of the results may then be obtained. Six images (channels) may be formed by separating $|H1(z,x)|$, $|H2(z,x)|$ and $|H3(z,x)|$ at the zero delay line ($z=0$). Channel 1 and Channel 2 are the images that represent the structural image of the sample. Channel 3 and Channel 4 are the images that represent the flow image without indication of flow directions. Channel 5 represents the flow image that indicates the flow moving toward or away from the incident probe beam. Channel 6 represents the flow image that indicates the flow moving opposite that in Channel 5.

In various embodiments, the first rectangle function $t1(k,f)$ may have the form:

$$t1(k,f) = \begin{cases} 1, & -F_0/2 < f \le F_0/2 \\ 0, & \text{Otherwise} \end{cases}$$

The second rectangle function $t2(k,f)$ may have the form:

$$t2(k,f) = \begin{cases} 0, & -F_0/2 < f \le F_0/2 \\ 1, & \text{Otherwise} \end{cases}$$

The third rectangle function $t3(k,f)$ may be of the form:

$$t3(k,f) = \begin{cases} 1, & f > F_0/2 \\ 0, & \text{Otherwise} \end{cases}$$

In various embodiments, the third rectangle function $t3(k,f)$ may also have the form:

$$t3(k,f) = \begin{cases} 1, & f < -F_0/2 \\ 0, & \text{Otherwise} \end{cases}$$

Figure 20:
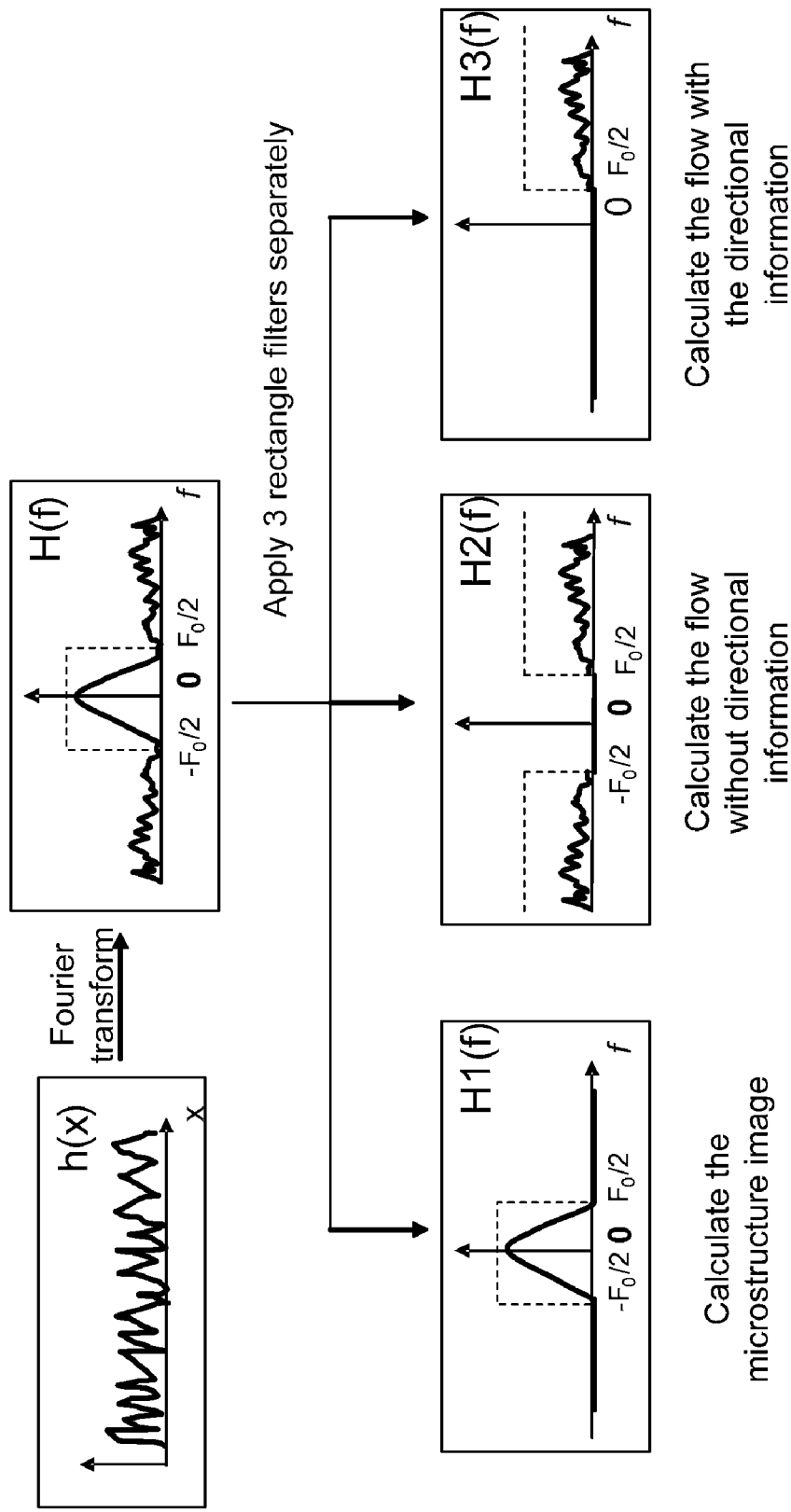
FIG. 20 schematically illustrates an embodiment of a rectangularly-shaped digital filtering method in accordance with various embodiments of the present invention.

An exemplary embodiment applying the rectangular filter functions is illustrated in FIG. 20, wherein a one dimensional function is used to aid in the understanding. As illustrated, the three rectangular functions are applied to a real interferogram function, h(x), which is extracted from h(k,x) at a particular wavenumber k.

Figure 21:
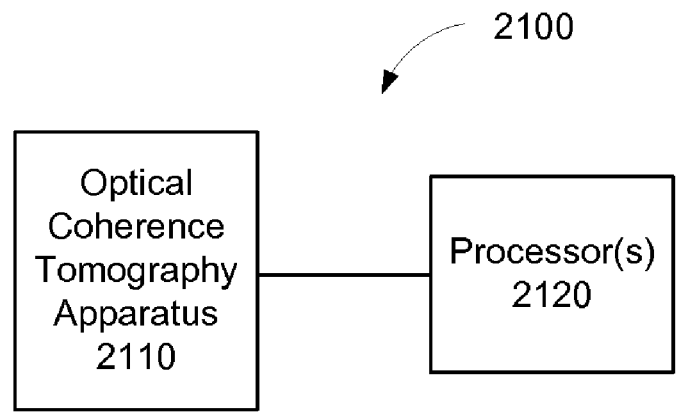
FIG. 21 illustrates an embodiment of an in vivo imaging system in accordance with various embodiments of the present invention.

Any one or more of various embodiments as previously discussed may be incorporated, in part or in whole, into a system. FIG. 21 illustrates an exemplary embodiment of an OCT system 2100. In the embodiments, OCT system 2100 may comprise an OCT apparatus 2110 and one or more processors 2120 coupled thereto. One or more of the processors 2120 may be adapted to perform methods in accordance with various methods as disclosed herein. In various embodiments, OCT system 2100 may comprise a computing apparatus including, for example, a personal computer, and in various ones of these embodiments, one or more of the processors may be disposed in the computing apparatus.

OCT systems in accordance with various embodiments may be adapted to store various information. For instance, an OCT system may be adapted to store parameters and/or instructions for performing one or more methods as disclosed herein.

In various embodiments, an OCT system may be adapted to allow an operator to perform various tasks. For example, an OCT system may be adapted to allow an operator to configure and/or launch various ones of the above-described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

Figure 22:
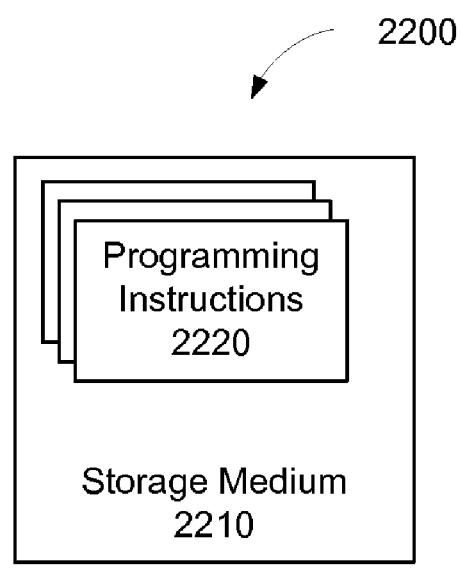
FIG. 22 illustrates an embodiment of an article of manufacture for in vivo imaging in accordance with various embodiments of the present invention.

Any one or more of various embodiments as previously discussed may be incorporated, in part or in whole, into an article of manufacture. In various embodiments and as shown in FIG. 22, an article of manufacture 2200 in accordance with various embodiments of the present invention may comprise a storage medium 2210 and a plurality of programming instructions 2220 stored in storage medium 2210. In various ones of these embodiments, programming instructions 2220 may be adapted to program an apparatus to enable the apparatus to perform one or more of the previously-discussed methods.

In various embodiments, an OCT image may provide data from which a diagnosis and/or evaluation may be made. In embodiments, such determinations may relate to biologic tissue structure, vasculature, and/or microcirculation. For example, in some embodiments, 3-D in vivo imaging of a biologic tissue and quantifying flow of blood through individual vessels therein may be useful in understanding mechanisms behind a number of disease developments and treatments including, for example, ischemia, degeneration, trauma, seizures, and various other neurological diseases. In still other embodiments, an OCT image and techniques herein disclosed may be used to identify cancer, tumors, dementia, and opthalmologic diseases/conditions (including, e.g., glaucoma, diabetic retinopathy, age-related macular degeneration). Still further, in various embodiments, OCT techniques as herein disclosed may be used for endoscopic imaging or other internal medicine applications. The foregoing illustrative embodiments of diagnosis and/or evaluation are exemplary and thus embodiments of the present invention are not limited to the embodiments discussed.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method of imaging, comprising:
   scanning a sample with an incident beam from a light source;
   detecting one or more spectral interference signals from the sample and a reference mirror;
   modulating the one or more spectral interference signals at a constant frequency while scanning the sample in a cross-sectional direction (B scan); and
   obtaining at least one image of the sample from the modulated one or more spectral interference signals, the at least one image including a full range structural image of the sample or a separated structure/flow image of the sample.

2. The method of claim 1, wherein said modulating comprises modulating the one or more spectral interference signals at a constant frequency.

3. The method of claim 1, wherein said obtaining at least one image comprises:
   separating structure information of the sample and flow information of the sample; and
   obtaining a first image and a second image, the first image including the structure information and the second image including the flow information.

4. The method of claim 1, wherein said scanning comprises scanning the sample with the incident beam in x and λ directions to obtain a first two-dimensional (2-D) spectral interferogram data set, said x direction including one or more columns and said λ direction including one or more rows.

5. The method of claim 4, wherein said obtaining the at least one image comprises:
   calculating discrete analytic functions, along the x-direction and row by row in the λ direction of the first 2-D data set, to obtain a complex valued function of the first 2-D data set; and
   converting the complex valued function of the first 2-D data set from a spectral domain to a time domain, column by column in the x direction, to obtain the at least one image of the sample.

6. The method of claim 5, wherein said calculating discrete analytic functions comprises Hilbert-transforming the first 2-D data set.

7. The method of claim 5, wherein said converting the complex valued function of the first 2-D data set comprises Fourier-transforming the complex valued function of the first 2-D data set.

8. The method of claim 4, further comprising scanning the sample with the incident beam in the x and λ directions along y direction to obtain a second 2-D spectral interferogram data set, said first and second 2-D data sets forming a three-dimensional spectral interferogram data set.

9. The method of claim 1, wherein said obtaining at least one image comprises obtaining the separated structure/flow image of the sample, and wherein the flow image of the sample is indicative of a direction of flow of the sample.

10. The method of claim 9, wherein a collection of all the B scans of the sample when the reference mirror moves toward the incident beam gives the flow away from the incident beam direction.

11. The method of claim 9, wherein a collection of all the B scans of the sample when the mirror moves away from the incident beam gives the flow toward the incident beam direction.

12. The method of claim 1, wherein the modulating comprises modulating the one or more spectral interference signals by a linear translation of the reference mirror.

13. The method of claim 1, wherein the modulating comprises modulating the one or more spectral interference signals by offsetting the incident beam.

14. The method of claim 1, wherein the modulating comprises modulating the one or more spectral interference signals by stretching an optical fiber providing the incident beam.

15. The method of claim 1, wherein the modulating at a constant frequency comprises modulating at a frequency having a constant value and a constant polarity.

16. A method for imaging, comprising:
   scanning a flowing sample with an incident beam from a light source;
   detecting one or more spectral interference signals from the flowing sample and a reference mirror;
   modulating digitally the one or more spectral interference signals from the flowing sample at a constant frequency;
   obtaining an image from the modulated one or more spectral interference signals, the image indicative of a direction of flow of the flowing sample.

17. The method of claim 16, wherein the digital modulation comprises:
   obtaining a cross-sectional data point from a flowing sample at a dimension of (x,λ), h(λ,x), at any one time;
   performing an interpolation for h(λ,x) from λ space to k space along the λ dimension column by column to obtain h(k,x);
   calculating a Fourier transform column by column along the λ dimension, resulting in H(z,x) that possesses positive and negative spaces in z;
   forming two functions from H(z,x) forcing negative space of H(z,x) equal to zero to form H1(z,x), and forcing positive space of H(z,x) equal to zero to form H2(z,x);
   modulating H1(z,x) and H2(z,x) digitally with a frequency of $f_0$ along the x dimension to obtain modulated signals H1'(z,x) and H2'(z,x);
   performing an inverse Fourier transformation to H1'(z,x) and H2'(z,x) along the z dimension and take only real parts or imaginary parts of results that form h1(k,x) and h2(k,x);
   calculating an analytic function along the x dimension row by row in the λ dimension to obtain a complex valued function of data from the inverse Fourier transformation operation resulting in $\hat{h}1(k,x)$ and $\hat{h}2(k,x)$;

performing a Fourier transformation of $\hat{h}1(k,x)$ and $\hat{h}2(k,x)$ along the k dimension to obtain complex optical images, H1(z,x) and H2(z,x) and obtain magnitudes of results; and separating |H1(z,x)| and |H2(z,x)| at zero delay line (z=0) to form four images of the flowing sample.

18. The method of claim 17, wherein two of said four images represent structural images of the flowing sample.

19. The method of claim 17, wherein one of said four images represents a flow image indicative of flow moving toward an incident probe beam.

20. The method of claim 17, wherein one of said four images represents a flow image indicative of flow moving away from an incident probe beam.

21. The method of claim 16, wherein the digital modulation comprises:
   obtaining a cross-sectional data point from a flowing sample at a direction of $(x,\lambda)$, $h(\lambda,x)$, at any one time;
   performing an interpolation for $h(\lambda,x)$ from $\lambda$ space to k space along an $\lambda$ direction column by column to obtain $h(k,x)$;
   calculating a Fourier transform row by row along an x direction, resulting in H(k,f) having positive and negative spaces in f;
   forming three functions from H(k,f) by:
      multiplying a first rectangle function t1(k,f) to form H1(k,f);
      multiplying a second rectangle function t2(k,f) to form H2(k,f); and
      multiplying a third rectangle function t3(k,f) to form H3(k,f);
   calculating analytic functions along an f direction row by row in k direction to obtain a complex valued function of the three functions resulting in $\hat{h}1(k,x)$, $\hat{h}2(k,x)$, and $\hat{h}3(k,x)$;
   performing a Fourier transformation of $\hat{h}1(k,x)$, $\hat{h}2(k,x)$, and $\hat{h}3(k,x)$ along the k direction to obtain the complex optical images, H1(z,x), H2(z,x), and H3(z,x) and obtain magnitudes of the images; and
   separating |H1(z,x)|, |H2(z,x)| and |H3(z,x)| at zero delay line (z=0) to form six images of the flowing sample.

22. The method of claim 21, wherein two of said six images represent structural images of the flowing sample.

23. The method of claim 21, wherein two of said six images represent flow images of the sample without indication of flow directions.

24. The method of claim 21, wherein one of said six images represents a flow image indicative of flow moving toward an incident probe beam.

25. The method of claim 21, wherein one of said six images represents a flow image indicative of flow moving away from an incident probe beam.

26. A system for in vivo imaging, comprising:
   an optical coherence tomography apparatus; and
   one or more processors coupled to the apparatus and adapted to cause the apparatus to:
      scan a sample with an incident beam from a light source;
      detect one or more spectral interference signals from the sample and a reference mirror;
      modulate the one or more spectral interference signals by a linear translation of a reference mirror while scanning the sample in a cross-sectional direction; and
      obtain at least one image of the sample from the modulated one or more spectral interference signals, the at least one image including a full range structural image of the sample or a separated structure/flow image of the sample.

27. The system of claim 26, wherein the optical coherence tomography apparatus includes a reference arm including a mirror mounted on a modulating device for modulating the one or more spectral interference signals.

28. The system of claim 26, wherein the one or more processors are adapted to cause the apparatus to scan the sample with the incident beam in x and $\lambda$ directions to obtain a first two-dimensional (2-D) spectral interferogram data set, said x direction including one or more columns and said $\lambda$ direction including one or more rows.

29. The system of claim 28, wherein the one or more processors are adapted to cause the apparatus to obtain the at least one image by:
   calculating discrete analytic functions, along the x-direction and row by row in the $\lambda$ direction of the first 2-D data set, to obtain a complex valued function of the first 2-D data set; and
   converting the complex valued function of the first 2-D data set from a spectral domain to a time domain, column by column in the x direction, to obtain the at least one image of the sample.

* * * * *